US012626796B2

(12) United States Patent
Shah et al.

(10) Patent No.: US 12,626,796 B2
(45) Date of Patent: May 12, 2026

(54) INTERACTIVE USER INTERFACE AND OPTIMIZED HEALTH PLAN RANKING

(71) Applicant: Healthline Media, LLC, Fort Mill, SC (US)

(72) Inventors: Munjal Shah, Plano, TX (US); Prafulla Krishna, Plano, TX (US); Bo Wang, Plano, TX (US); Vishal Parikh, Plano, TX (US); Michael Gunn, Plano, TX (US); Jane Fu, Plano, TX (US); Alex Miller, Plano, TX (US); Chander Sudanthi, Plano, TX (US); Raj Vavilala, Plano, TX (US); Sebastian Bierman-Lytle, Plano, TX (US)

(73) Assignee: Healthline Media, LLC, Fort Mill, SC (US)

( * ) Notice: Subject to any disclaimer, the term of this patent is extended or adjusted under 35 U.S.C. 154(b) by 77 days.

(21) Appl. No.: 17/984,905

(22) Filed: Nov. 10, 2022

(65) Prior Publication Data

US 2023/0282325 A1      Sep. 7, 2023

Related U.S. Application Data

(60) Provisional application No. 63/403,193, filed on Sep. 1, 2022, provisional application No. 63/326,076, filed
(Continued)

(51) Int. Cl.
G16H 15/00 (2018.01)
G16H 10/60 (2018.01)
(Continued)

(52) U.S. Cl.
CPC ............. G16H 15/00 (2018.01); G16H 10/60 (2018.01); G16H 20/00 (2018.01); G16H 20/10 (2018.01);
(Continued)

(58) Field of Classification Search
CPC ........ G16H 15/00; G16H 10/60; G16H 20/00; G16H 20/10; G16H 40/63; G16H 50/20;
(Continued)

(56) References Cited

U.S. PATENT DOCUMENTS 5,572,421 A      11/1996  Altman et al.
5,639,471 A      6/1997   Chait
(Continued)

FOREIGN PATENT DOCUMENTS

CA      2887411      10/2015
CN      105760692 A      7/2016
(Continued)

OTHER PUBLICATIONS

Blue Button API Docs, 2020, https://web.archive.org/web/20200414013433/https://bluebutton.cms.gov/developers/#fhir-data-model (Year: 2020).*
(Continued)

*Primary Examiner* — Mamon Obeid
*Assistant Examiner* — Andrew Kyle Tapia
(74) *Attorney, Agent, or Firm* — Potomac Law Group, PLLC; Jamaica Potts Szeliga

(57)      ABSTRACT
A computing system can obtain health record data of a user from a number of health record sources, and generate, on a computing device of the user, an interactive user interface comprising prepopulated data based on the health record data. Based on interactions by the user on the interactive user interface, the system can receive input data from the computing device of the user, the input data corresponding to health-related information provided by the user. Based on at least one of the health record data or the input data, the system can generate a set of health outcome predictions for the user, and based on the set of health outcome predictions,
(Continued)

the input data, and the health record data, the system can generate a set of health care plan rankings for the user.

20 Claims, 21 Drawing Sheets

Related U.S. Application Data on Mar. 31, 2022, provisional application No. 63/277, 889, filed on Nov. 10, 2021.

(51) Int. Cl.

| | |
|---|---|
| *G16H 20/00* | (2018.01) |
| *G16H 20/10* | (2018.01) |
| *G16H 40/63* | (2018.01) |
| *G16H 50/20* | (2018.01) |
| *G16H 50/30* | (2018.01) |
| *G16H 50/50* | (2018.01) |
| *G16H 70/20* | (2018.01) |
| *G16H 70/40* | (2018.01) |
| *G16H 70/60* | (2018.01) |
| *H04M 3/51* | (2006.01) |

(52) U.S. Cl.
CPC ............. *G16H 40/63* (2018.01); *G16H 50/20* (2018.01); *G16H 50/30* (2018.01); *G16H 50/50* (2018.01); *G16H 70/20* (2018.01); *G16H 70/40* (2018.01); *G16H 70/60* (2018.01); *H04M 3/5158* (2013.01)

(58) Field of Classification Search
CPC ........ G16H 50/30; G16H 50/50; G16H 70/20; G16H 70/40; G16H 70/60; G16H 40/20; H04M 3/5158
See application file for complete search history.

(56) References Cited

U.S. PATENT DOCUMENTS

| | | | |
|---|---|---|---|
| 5,711,297 | A | 1/1998 | Iliff |
| 5,879,163 | A | 3/1999 | Brown |
| 6,151,581 | A | 11/2000 | Kraftson |
| 7,319,970 | B1 | 1/2008 | Simone |
| 9,727,885 | B1 | 8/2017 | Reier |
| 10,878,062 | B1 | 12/2020 | Garavaglia et al. |
| 11,412,088 | B1 | 8/2022 | Collins et al. |
| 2002/0004727 | A1 | 1/2002 | Knaus et al. |
| 2002/0035486 | A1 | 3/2002 | Huyn et al. |
| 2003/0027122 | A1 | 2/2003 | Stansvik |
| 2003/0177032 | A1 | 9/2003 | Bonissone |
| 2003/0195772 | A1 | 10/2003 | Meek |
| 2005/0102171 | A1 | 5/2005 | Ashley |
| 2005/0182659 | A1 | 8/2005 | Huttin |
| 2005/0228692 | A1 | 10/2005 | Hodgdon |
| 2005/0234742 | A1 | 10/2005 | Hodgdon |
| 2006/0155581 | A1 | 7/2006 | Eisenberger et al. |
| 2007/0005396 | A1 | 1/2007 | Lee |
| 2007/0061166 | A1 | 3/2007 | Ramasubramanian |
| 2007/0118398 | A1 | 5/2007 | Perls |
| 2007/0129611 | A1 | 6/2007 | Ratka |
| 2008/0046292 | A1 | 2/2008 | Myers et al. |
| 2008/0133273 | A1 | 6/2008 | Marshall |
| 2008/0147441 | A1 | 6/2008 | Kil |
| 2008/0177569 | A1 | 7/2008 | Chen et al. |
| 2009/0055915 | A1 | 2/2009 | Piliouras |
| 2009/0111085 | A1 | 4/2009 | Rudy |
| 2009/0241028 | A1 | 9/2009 | Iskedjian |
| 2010/0004947 | A1 | 1/2010 | Nadeau |
| 2010/0191544 | A1* | 7/2010 | Bosworth .............. G16H 70/20 |
| | | | 715/709 |
| 2011/0022420 | A1 | 1/2011 | Morse |
| 2011/0046985 | A1 | 2/2011 | Raheman |

| | | | |
|---|---|---|---|
| 2011/0307311 | A1 | 12/2011 | Turgiss |
| 2012/0004925 | A1 | 1/2012 | Braverman |
| 2012/0016692 | A1* | 1/2012 | Jenkins-Robbins ... G06Q 40/08 |
| | | | 705/4 |
| 2012/0041788 | A1 | 2/2012 | Wons |
| 2012/0123802 | A1 | 5/2012 | Feldman |
| 2012/0123809 | A1 | 5/2012 | Read |
| 2012/0156664 | A1 | 6/2012 | Hurwitz |
| 2012/0251993 | A1 | 10/2012 | Chidambaran et al. |
| 2013/0024212 | A1 | 1/2013 | Atakhorrami |
| 2013/0035207 | A1 | 2/2013 | Abuelsaad |
| 2013/0096942 | A1 | 4/2013 | Bowles |
| 2013/0117040 | A1 | 5/2013 | James et al. |
| 2013/0138450 | A1 | 5/2013 | Vigneux |
| 2013/0211858 | A1 | 8/2013 | Ohnemus |
| 2013/0230841 | A1 | 9/2013 | Bremer |
| 2013/0291098 | A1 | 10/2013 | Chung |
| 2013/0332189 | A1 | 12/2013 | Manning |
| 2014/0087355 | A1 | 3/2014 | Henry |
| 2014/0156308 | A1 | 6/2014 | Ohnemus |
| 2014/0214441 | A1 | 7/2014 | Young |
| 2014/0244305 | A1 | 8/2014 | Schoenberg |
| 2014/0257852 | A1 | 9/2014 | Walker |
| 2014/0278474 | A1 | 9/2014 | McClure |
| 2014/0316811 | A1 | 10/2014 | Ohnemus |
| 2014/0350961 | A1 | 11/2014 | Csurka et al. |
| 2014/0372133 | A1 | 12/2014 | Austrum |
| 2015/0019266 | A1 | 1/2015 | Stempora |
| 2015/0046174 | A1 | 2/2015 | Mainwaring |
| 2015/0104759 | A1 | 4/2015 | Block |
| 2015/0161538 | A1 | 6/2015 | Matus |
| 2015/0161738 | A1 | 6/2015 | Stempora |
| 2015/0178920 | A1 | 6/2015 | Garnavi et al. |
| 2015/0254754 | A1* | 9/2015 | Lang ..................... G06Q 40/08 |
| | | | 705/4 |
| 2015/0278958 | A1* | 10/2015 | Brunner ................. H04N 5/222 |
| | | | 705/3 |
| 2015/0317650 | A1 | 11/2015 | Mahoney |
| 2016/0049084 | A1 | 2/2016 | Chamberlain |
| 2016/0086505 | A1 | 3/2016 | Hanlon |
| 2016/0110815 | A1 | 4/2016 | Dellaripa |
| 2016/0140310 | A1 | 5/2016 | Jiao et al. |
| 2016/0140323 | A1 | 5/2016 | Jiao et al. |
| 2016/0140642 | A1 | 5/2016 | Jiao et al. |
| 2016/0140859 | A1 | 5/2016 | Jiao et al. |
| 2016/0188813 | A1 | 6/2016 | Hennenfent |
| 2016/0203284 | A1 | 7/2016 | Ouyan |
| 2016/0210427 | A1 | 7/2016 | Mynhier et al. |
| 2016/0246947 | A1 | 8/2016 | Yao |
| 2016/0335404 | A1 | 11/2016 | Srinivas |
| 2017/0001190 | A1 | 1/2017 | Ito |
| 2017/0103179 | A1 | 4/2017 | Jiao et al. |
| 2017/0103180 | A1 | 4/2017 | Jiao et al. |
| 2017/0103469 | A1 | 4/2017 | Jiao et al. |
| 2017/0109829 | A1 | 4/2017 | Amigo |
| 2017/0132396 | A1 | 5/2017 | Bechtold |
| 2017/0193165 | A1 | 7/2017 | Mandalika |
| 2017/0235887 | A1* | 8/2017 | Cox ..................... G16H 10/60 |
| | | | 705/3 |
| 2017/0262603 | A1 | 9/2017 | Grow et al. |
| 2018/0144829 | A1 | 5/2018 | Cantor |
| 2018/0165062 | A1 | 6/2018 | Yoo et al. |
| 2018/0268106 | A1 | 9/2018 | Velaga |
| 2018/0294048 | A1 | 10/2018 | Blumenthal et al. |
| 2018/0358117 | A1 | 12/2018 | Neagle |
| 2019/0026364 | A1 | 1/2019 | Sankovsky |
| 2019/0080370 | A1 | 3/2019 | Copeland et al. |
| 2019/0095590 | A1 | 3/2019 | Knoop |
| 2019/0139146 | A1 | 5/2019 | Sato et al. |
| 2019/0180852 | A1 | 6/2019 | Jiao et al. |
| 2019/0304023 | A1* | 10/2019 | Pingali ................... G16H 50/30 |
| 2019/0341154 | A1* | 11/2019 | Kapur ................... G06Q 40/08 |
| 2020/0020038 | A1 | 1/2020 | Haile |
| 2020/0134691 | A1* | 4/2020 | Wiseman, Sr. .... G06Q 30/0633 |
| 2020/0251189 | A1 | 8/2020 | Jiao et al. |
| 2020/0251221 | A1 | 8/2020 | Jiao et al. |
| 2020/0251222 | A1 | 8/2020 | Jiao et al. |
| 2021/0020307 | A1* | 1/2021 | Bhimavarapu .... G06Q 10/1097 |
| 2021/0082056 | A1 | 3/2021 | Hirobe |

(56) References Cited

U.S. PATENT DOCUMENTS

| | | | |
|---|---|---|---|
| 2021/0135841 A1* | 5/2021 | Lee | G06F 21/6245 |
| 2021/0192454 A1 | 6/2021 | Jiao et al. | |
| 2021/0210176 A1 | 7/2021 | Jiao et al. | |
| 2021/0225469 A1 | 7/2021 | Valdes et al. | |
| 2021/0383932 A1 | 12/2021 | Kobetz | |
| 2021/0391075 A1 | 12/2021 | Marks et al. | |
| 2022/0058339 A1* | 2/2022 | Archuleta | G06N 3/084 |
| 2022/0114674 A1 | 4/2022 | Hinchey | |
| 2023/0162825 A1 | 5/2023 | Nanduri et al. | |

FOREIGN PATENT DOCUMENTS

| | | |
|---|---|---|
| CN | 108734592 | 11/2018 |
| JP | 2002123612 | 4/2002 |
| JP | 2013524332 | 6/2013 |
| KR | 10-2016-0050573 A | 5/2016 |
| SG | 10201902514 W | 8/2020 |
| WO | WO-2011/058463 A2 | 5/2011 |
| WO | WO-2016/050990 A1 | 4/2016 |
| WO | WO-2016/077781 | 5/2016 |
| WO | WO-2018/057798 | 3/2018 |
| WO | WO-2019/202707 | 10/2019 |
| WO | WO2021/0262609 | 12/2021 |

OTHER PUBLICATIONS

International Search Report and Written Opinion from PCT Application No. PCT/US2015/060723, mailed Feb. 4, 2016, 9 pages.
Notification Concerning Transmittal of International Preliminary Report on Patentability PCT Application No. PCT/US2015/060723, mailed May 26, 2017, 8 pages.
International Search Report and Written Opinion from PCT Application No. PCT/US2017/052804, mailed Dec. 7, 2017, 7 pages.
Prokoshfna N.R. Prognozirovanie otnositelnogo riska obschey smertnosti u lits s arterialnoy gipertenziey (po dannym desyatiletnego kogortnogo issledovaniya). Vestnik Vitebskogo gosudarstvennogo meditsinskogo universiteta, 2011, pp. 54-62 Abstract in English.
Batura T.V. Programmnye produkty i sistemy. Nauchno-Prakticheskoe izdanie. Tver 2013, X2 3 (103), pp. 130-137 Abstract in English.
European Search Report dated Jul. 23, 2018, Application No. 15859764.1 8 pages.
Office Action dated Oct. 1, 2019, Japanese Application No. 2017-526588, 12 pages.
Karen B. DeSalvo et al., Mortality Prediction with a Single General Self-Rated Health Question, Journal of General Internal Medicine 21:3, pp. 267-275 (Mar. 2006), https://onlinelibrary.wiley.com/doi/full/10.111/j.1525-1497.2005.00291.x (last visited on Sep. 25, 2019) (Year:2006).
European Examination Report dated Dec. 11, 2019, Application No. 15859764.1 11 pages.
European Search Report dated Feb. 11, 2020, Application No. 17853933.4 11 pages.
Office Action dated Jun. 9, 2020, Japanese Application No. 2017-526588, 6 pages.
Australian Examination Report dated Jul. 28, 2020, Application No. 2015346070 3 pages.
International Search Report and Written Opinion from PCT Application No. PCT/US2021/038287, mailed Sep. 15, 2021, 10 pages.
International Search Report and Written Opinion from PCT Application No. PCT/US2021/054178, mailed Jan. 13, 2022, 13 pages.
Australian Examination Report dated Jan. 12, 2022, Application No. 2017331252 4 pages.
European Examination Report dated Nov. 3, 2022, Application No. 17853933.4 14 pages.
Australian Examination Report dated Oct. 20, 2022, Application No. 2021209244 4 pages.
Mercado, J. (2020, Dec. 14), Blue Button 2.0: Everything you need to know and more!. CareJourney. https://carejourney.com/blue-button-2-0-everything-you-need-to-know-and-more/ (Year:2020).
Rea et al., Building a robust, scalable and standards-driven infrastructure for secondary use of EHR data: The SHARPn project, Aug. 2012, Journal of Biomedical Informatics, vol. 45, Iss. 4, pp. 763-771.

* cited by examiner

| User: Jane Doe | Script Interface 500 |
|---|---|
| DOB – 08/25/1957 (Age 69)<br>Loc. – Akron, OH | Dynamic Script 505<br><br>Agent Angela: "I'm calling to discuss your pending Medicare eligibility and to see if you'd like to explore the best options given your current situation. Are you interested?" |
| - 2 sons<br>-- Carl 40 yo, Cleveland, OH<br>-- Jeff 37 yo, New York City, NY | |
| Health Record Data 515<br>  Diagnoses:<br><br><br><br><br><br>  Prescriptions: | Agent Angela: "I'm so happy to hear that. Sounds nice out there."<br><br>Agent Angela: "How is the weather in Akron?"<br><br>Agent Angela: "Hello, Mrs. Doe, how are you doing this morning?" |
| | Health Plan Rankings 510<br><br>1. HMO 45625<br><br>2. HMO 96726<br><br>3. SNP 33689<br><br>4. PFFS 4424 |
| Income:<br>Pension - $XXXX/yr | 5. PPO 34546 |

*FIG. 5A*

| User: Jane Doe | Script Interface 500 |
|---|---|
| DOB – 08/25/1957 (Age 69)<br>Loc. – Akron, OH | Dynamic Script 505<br><br>Agent Angela: "We should discuss a gap in your current coverage and whether you'd like to close it." |
| - 2 sons<br>-- Carl 40 yo, Cleveland, OH<br>-- Jeff 37 yo, New York City, NY | Agent Angela: "How do you feel about your current plan?" |
| Health Record Data 515<br>  Diagnoses:<br>- Diabetes<br>- Broken tibia<br>- Carpal Tunnel<br>- Hypertension<br>- Chronic Stress<br><br><br>  Prescriptions:<br>- Antianxiety B<br>- HYDCHLTHZD<br>- Insulin<br>- Simvastatin | Agent Angela: "Thanks so much, we're obtaining them as we speak."<br><br>Agent Angela: "Will you provide authorization to access your health records?"<br><br>Agent Angela: "I'm calling to discuss your pending Medicare eligibility and to see if you'd like to explore the best options given your current situation. Are you |
|  | Health Plan Rankings 510<br><br>1. SNP 33689<br><br>2. PFFS 4424<br><br>3. PPO 34546<br><br>4. HMO 45625 |
| Income:<br>Pension - $XXXX/yr | 5. HMO 96726 |

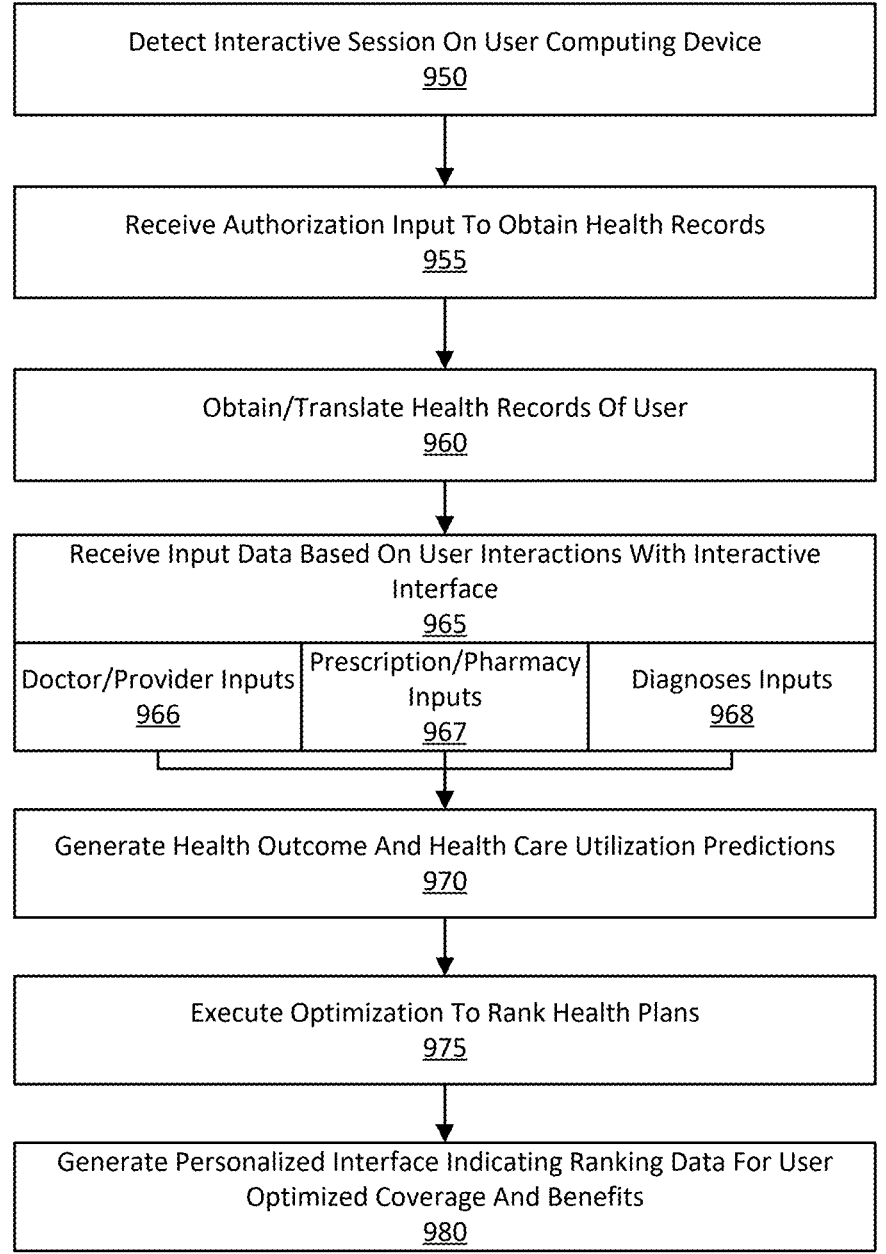

Detect Interactive Session On User Computing Device
950

Receive Authorization Input To Obtain Health Records
955

Obtain/Translate Health Records Of User
960

Receive Input Data Based On User Interactions With Interactive Interface
965

| Doctor/Provider Inputs 966 | Prescription/Pharmacy Inputs 967 | Diagnoses Inputs 968 |
|---|---|---|

Generate Health Outcome And Health Care Utilization Predictions
970

Execute Optimization To Rank Health Plans
975

Generate Personalized Interface Indicating Ranking Data For User Optimized Coverage And Benefits
980

*FIG. 9B*

INTERACTIVE USER INTERFACE AND OPTIMIZED HEALTH PLAN RANKING

CROSS-REFERENCE TO RELATED APPLICATIONS

This application claims the benefit of priority to each of U.S. Provisional Application No. 63/277,889, filed on Nov. 10, 2021, U.S. Provisional Application No. 63/326,076, filed on Mar. 31, 2022, and U.S. Provisional Application No. 63/403,193, filed on Sep. 1, 2022; the aforementioned priority applications being hereby incorporated by reference in their respective entireties.

BACKGROUND

Health record access is typically provided through individual health care providers, healthcare organizations, insurance companies, pharmacies, pharmacy benefit managers, and others. It is nearly impossible for any individual to construct and access a central record repository from these disparate sources. Health care services are provided by health care providers through health care plans, which can vary in coverage, cost, deductibles, quality, and copays. Individuals are typically tasked with obtaining their own health care plans.

Call sessions between users and call agents for health care services may require extensive information gathering and verification of personal health and medical history information to enable a system to determine an optimal health care plan for the user. Such information gathering and verification can correspond to the user's personal information and medical history (e.g., past medical conditions, current medical conditions, past and current prescriptions, diagnoses, and the like).

BRIEF DESCRIPTION OF THE DRAWINGS

The disclosure herein is illustrated by way of example, and not by way of limitation, in the figures of the accompanying drawings in which like reference numerals refer to similar elements, and in which:

FIGS. 5A and 5B are example script interfaces presented to a call agent during a call session with a user, according to various examples;

FIGS. 8E through 8H depict example interactive user interfaces presented to users to implement one or more processes described herein;

FIG. 9B is a flow chart describing another method of optimizing health plans for users, according to various examples;

DETAILED DESCRIPTION

Figure 1:
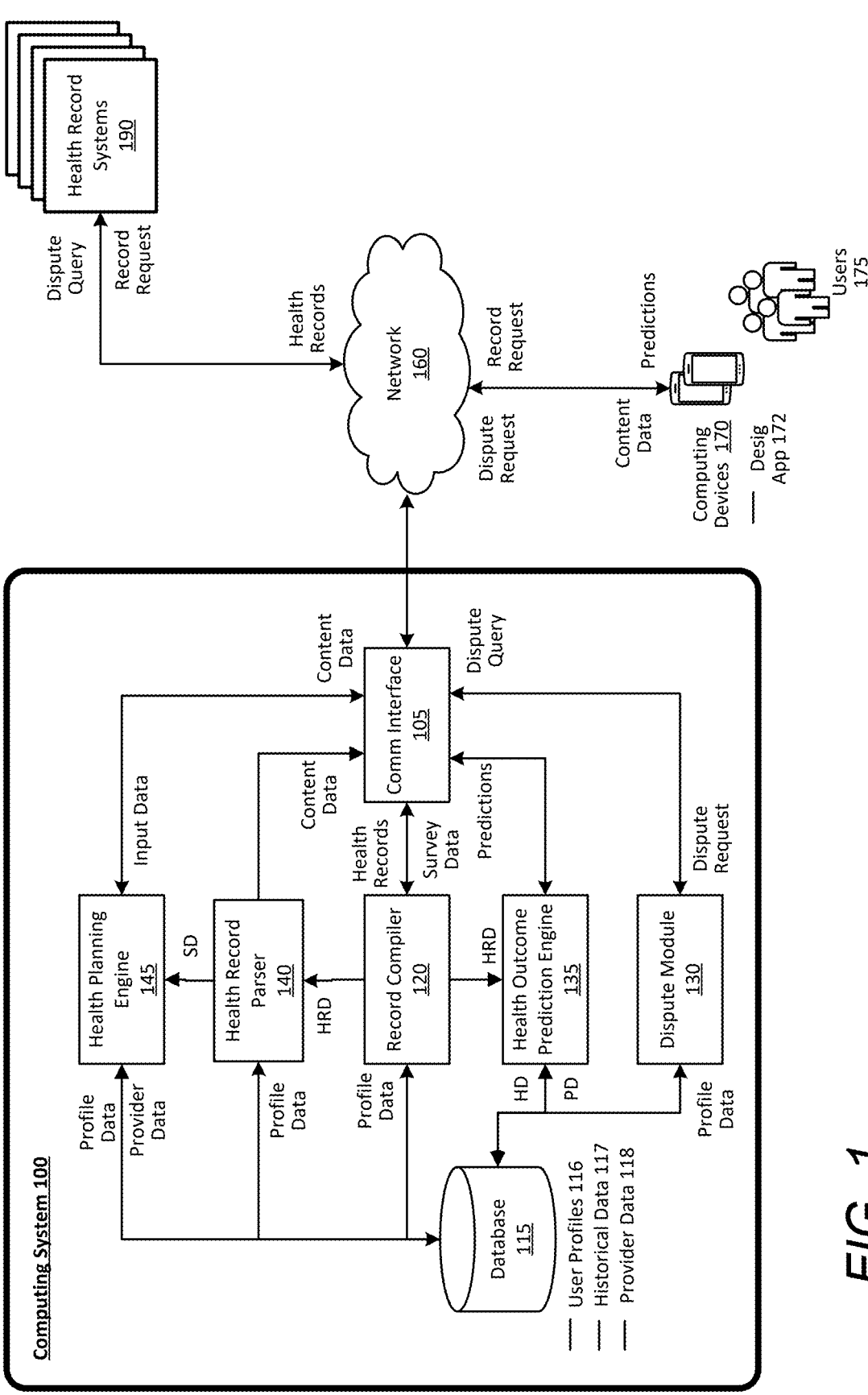
FIG. 1 illustrates computing system implementing health prediction and planning service for users, in accordance with examples described herein.

A computing system can compile health records for users that may encompass all of the users' health care visits, diagnoses, treatments, prescriptions, test results, insurance claims, and other health-related information. In certain implementations, a user can access the health records via an executing application on the user's computing device or via website through a browser. In some examples, the user can set up an account with the computing system and provide credential information, such as a username or a phone number with a link, code or password. Using the credential information, the user can log into the system to initially access health record information from a plurality of health record systems, such as hospital appointment and/or visit records, diagnosis information, treatment information, prescription information, past health procedures (e.g., surgeries, screening, tests, etc.), and the like.

Upon receiving a health record request from a user, the computing system can utilize the credential information of the user to access the health record systems of each health service provider of the user and/or the insurance claims and vendor databases that contain the user's health data, and obtain the user's health records. It is contemplated that the health records of the user may comprise technical terms or codes (e.g., current procedure terminology (CPT) codes, health common procedure coding system (HCPCS) codes, internal classification of diseases (ICD) codes, internal classification of functioning, disability, and health (ICF) codes, diagnostic-related group (DRG) codes, national drug codes (NDC codes), code on dental procedures and nomenclature (CDT), diagnostic and statistical manual of mental disorder (DSM) codes, generic and brand drug names, medical terminology for diagnoses and procedures, hierarchical condition category (HCC) scores, risk adjustment factor (RAF) scores, national council for prescription drugs (NCPDP) and national provider identifier (NPI) codes, etc.) that may be difficult or impractical for a typical user to decipher.

According to examples provided herein, the computing system can process and translate the health records of the user to generate an individualized user interface (e.g., an app interface or web browser interface) that provides the user with plain language summaries of the user's health records. For example, each health record may be categorized based on type (e.g., procedures, diagnoses, prescriptions, treatment plans, etc.), and classified based on one or more additional criteria (e.g., by doctor, by date, by health insurance provider, by health care service location or area (e.g., hospital address), etc. In various implementations, the computing system can initiate a health record verification process with the user to verify that the user's health records are complete and accurate.

For example, in an initial verification process, the computing system can present the user with a set of interactive content features that query the user of whether a set of health records are accurate (e.g., if the user remembers a hospital stay, a prescription, or procedure). When presented with plain language information corresponding to a particular health record, if the user is unable to remember or requires more information, the computing system can present the user with additional contextual information associated with the health record, such as an image of a prescription drug, a non-generic brand name(s) of an equivalent drug, the generic name of an equivalent drug, an address of a health care facility, last fill date, last prescriber, and the like, in order to stimulate the user's memory.

In further implementations, the computing system can process the user's health records to identify any anomalies or records that do not appear consistent with other records or which may have potential for user harm. For example, a user may have a set of health records consistent with a current set of diagnoses, prescriptions, and/or treatment plans, and the computing system may identify an anomalous health record indicating an inconsistent prescription for a drug that may have an adverse reaction to another drug the user has been prescribed. In such an example, the computing system may prioritize the verification of such anomalous health records for the user.

In certain examples, the user may input additional information for a particular health record, such as a frequency of use for a prescription or over-the-counter medication. In such examples, the computing system may prompt the user to provide additional information that may be useful for the various health-related services described herein. Furthermore, the user may be provided with comprehensive access to health data from all of the user's providers, a feature that is not readily possible with current implementations. It is contemplated that enabling users to provide additional contextual information regarding their health care can make up for lack of context in current insurer coding procedures for record-keeping, and can also provide the system with additional information not available in current insurer records, such as use of over-the-counter drugs, supplements, dietary information, etc., which can be processed by the system to determine factors such as adverse drug interactions.

When a health record is disputed by the user, the computing system can initiate a dispute process to reconcile the disputed record. In certain implementations, the computing system can provide forms and/or links to guide the user through the dispute process with a relevant health record system to resolve the discrepancy. In such implementations, the computing system provides via the user interface all necessary documents that the user is to fill out and can guide the user in submitting the documents to the correct entities. In further examples, the computing system can create a set of content features that enables the user to provide all necessary information, and automatically fills out the necessary documents for submission. In such examples, the computing system can act as a dispute portal that enables the user to provide the necessary information and submit the documents via the user interface presented on the executing application or website.

The dispute process can be performed for any type of health record dispute. For example, during the health record verification process, the user may be tasked with reviewing the user's healthcare providers (e.g., physicians, nurses, nurse practitioners, physician's assistants dentists, podiatrists, pharmacists, etc.), pharmacies, diagnoses, medical procedures, prescriptions, visited health care facilities, health insurance providers, and the like. As an example, the user may dispute a medical record indicating that the user has visited a particular healthcare provider, or a request an amendment to a medical record indicating that the user has been prescribed with a particular drug. The computing system can facilitate the user in configuring a dispute request, submitting the necessary information to the relevant health record system, performing any further back-and-forth communications, and ultimately resolve each disputed health record.

It is contemplated that subsequent to the health record verification and dispute resolution processes, the user will have a more accurate and complete health record that enables health service providers to provide highly tailored risk mitigation products and health care services for the user. In various implementations, the computing system can continually receive updated health information from its userbase, and compile a historical record of health information for each user. In further implementations, the computing system can execute health correlation and prediction logic on the historical data to identify various combinations of symptoms, diagnoses, prescription medications, treatments, health care quality (e.g., individual doctors), etc. to identify, for any given user, a set of potential health risks that the user faces given the user's current health information.

For example, the computing system can process a user's health record information and identify any adverse factors, such as prescription and over the counter drugs that may have adverse reactions or a current treatment program for one medical condition that may be adverse to a different medical condition of the user's. For any adverse factors in the user's health records, the computing system can provide an alert to the user and any informational material indicating studies or current medical research indicating or describing the adverse factor. The computing system may further predict a set of future health outcomes of the user given the user's current health record and current health trajectory, and in certain examples, provide the user with individually tailored information (e.g., a newsletter or medical publications) that may provide the user with greater awareness of the current and predicted health risks and outcomes accordingly.

In various implementations, the computing system can execute planning and recommendation logic to individually tailor health care planning for the user based on the user's verified health record information. For example, based on the predicted health risks or outcomes for the user, the computing system can utilize historical health care data to provide the user with financial planning recommendations, diet and exercise recommendations, optimal health care and risk mitigation plans (e.g., an optimal health insurance policy and one or more optimal doctors), lifestyle recommendations (e.g., whether the user should move to a location at which family members may be readily available), optimal health care facilities, and the like. The historical health care data can provide an indication of anticipated health care costs for the user based on the predictions, and can enable the computing system to optimize a health care plan for the user in order to, for example, minimize the anticipated costs while providing the user with adequate or superior care.

In various implementations, the computing system can further provide risk mitigation plan recommendations based on the user's health history. For example, users may be provided with Medicare plan recommendations, as well as auto insurance and life insurance plan recommendations. Other users may also be provided with non-Medicare insurance plan recommendations based on their individual health record information. In further implementations, the computing system can provide doctor recommendations based on the user's current or predicted health risks. For example, if the user is predicted to have a particular health issue or currently has a particular health issue (e.g., diabetes, skin cancer), then given the user's health insurance coverage, the computing system can provide the user with a list of doctors that specialize in the health issue and/or have been surveyed to be in a top percentile of doctors for the health issue, including but not restricted to specific health outcome metrics (e.g., medical and surgical error rates).

In further implementations, the computing system can provide a social support network by matching users with other users experiencing similar health issues or having similar health risks. For example, based on the user's predicted and/or actual health risks and diagnoses, the computing system can identify one or more additional users, and provide a notification to each of the user's indicating the match. In some aspects, the matched users can be provided with messaging and other contact methods to provide the users with a social support platform for those dealing with similar health issues.

Additionally, the computing system can continuously update a central repository that comprises the health records from all health record sources for the user. In one example, the computing system automatically polls the health record databases for any updated information for the user, such as new health care visits, prescriptions, and diagnoses. In additional examples, the computing system can further update a catalog of health-related literature based on current or recently conducted research, clinical trials, and treatments that may be relevant to the user. Accordingly, if the user qualifies for a particular clinical trial or research program, the computing system can transmit a notification indicating the clinical trial or research program to the user's computing device to enable the user to participate in the clinical trial or research program. It is contemplated that this information may be of particular interest to clinical sponsors and research programs.

In various examples, the computing system can utilize user reviews (e.g., survey data of health care providers, insurers, physicians, etc.), the health records of users, and the outcomes and progressions of their diseases to predict ratings of various health care providers and insurers (e.g., star ratings of Medicare providers). Furthermore, by providing a central repository of user health records and the various health services described herein, the system may facilitate in driving higher adherence by reminding the user to fill and take drugs as prescribed, to schedule medical appointments and visit their doctors, to adhere to medical tests, and the like. The system can further facilitate in medical therapy management for users, which can comprise an extension of adverse drug monitoring and adherence monitoring.

Examples described herein achieve a technical effect of integrating the health records of users from multiple health data systems in a single application-based service to provide individually tailored health services. Current embodiments typically require patients to access each of the user's health care providers through individual portals of each health care provider. Using secure network technology—enabling access to hospital systems, insurer portals, pharmacies and pharmacy benefit management systems, government portals, healthcare enterprise resource planning (ERP) systems, Blue Button APIs, and other databases—the computing system described herein can provide the user with a single, integrated health care portal for all of the user's health care providers. In doing so, the computing system can utilize the corpus of the user's health records—as well as historical health data relating to health risks, health care, costs, diagnoses, and treatments—to optimize health and risk mitigation services of the user.

In further examples, a computing system can execute a customer relations management system to implement dynamic assistance for call agents, particularly during health coverage plan calls with users requiring health care coverage or wishing to improve upon their current health care coverage or other related health care service offerings. In various implementations, the computing system can receive survey data corresponding to current patient experiences with their current health care plans. The survey data can indicate whether the patients are satisfied with their plans and which aspects or benefits of their plans could be improved upon (e.g., copays, deductibles, assigned or selected doctors, health care facilities, prescriptions, health care quality, etc.). The survey data can be obtained over time to improve upon the computing system's current capabilities (e.g., machine learning capability) in providing optimal health care coverage recommendations, along with additional personal information of a user (e.g., the user's health care records and history, demographic information, preferences, location, age, and the like).

In some examples, the computing system can obtain publicly available, third-party information of potential users, or can obtain permissions from potential users to acquire information such as, but not limited to, household income, household size, demographic information, age and gender of household members, home locations, social media information (e.g., indicating lifestyle), and the like. The computing system can utilize this information to identify potential users that may wish to update their health care coverage. In further examples, the computing system may also obtain the health records of a potential user—given the appropriate authorizations from the user—to further identify potential users that may wish to update their health care coverage. The computing system can process the survey data, third-party information, and/or health record information of the potential users in order to prioritize contact lists for call agents associated with a health care service implemented by the computing system.

In additional examples, the user may take a cognitive assessment test prior to a call session with a call agent, which can be monitored and processed by the computing system to determine the cognitive abilities of the user, such as, but not limited to, spatial reasoning, motor function, word finding, and language processing abilities for the user. Further description of the cognitive assessment test may be found in PCT Application No. WO2021/262609 A1, titled "Computing System Implementing a Cognitive-Based Risk Assessment Service for Motor Vehicle Risk Determination," filed on Jun. 21, 2021, which is incorporated herein by reference in its entirety. As described herein, the results of the cognitive assessment test can be utilized by the computing system for dynamic scripting purposes in a call session between the user and a call agent, along with the additional information described below.

As provided herein, prior to or during a call session with a call agent, the user can provide certain information for processing by the computing system. For example, the user may provide authorizations (e.g., during a call session or via a website prior to a call session) to enable the computing system to obtain the user's health records from any number of health care sources. These health records can include, without limitation, the user's history of health care visits, diagnoses, treatments, prescriptions, test results, insurance claims, and other health-related information. In some examples, the user can set up an account with the computing system and provide credential information, such as, but not limited to, a username or a phone number with a link, code, or password. Additionally or alternatively, the user can provide any permissions and/or credentials during a call session with the call agent. Using the credential information, the computing system can access health record information from a plurality of health record systems, such as, but not limited to, hospital appointment and/or visit records, diagnosis information, treatment information, prescription information, past health procedures (e.g., surgeries, screening, tests, etc.), and the like.

In various implementations, the computing system can utilize the credential information of the user to access the health record systems of each health service provider of the user and/or the insurance claims and vendor databases that contain the user's health data, and obtain the user's health records. It is contemplated that the health records of the user may comprise technical terms or codes (e.g., current procedure terminology (CPT) codes, health common procedure coding system (HCPCS) codes, internal classification of diseases (ICD) codes, internal classification of functioning, disability, and health (ICF) codes, diagnostic-related group (DRG) codes, national drug codes (NDC codes), code on dental procedures and nomenclature (CDT), diagnostic and statistical manual of mental disorder (DSM) codes, generic and brand drug names, medical terminology for diagnoses and procedures, hierarchical condition category (HCC) scores, risk adjustment factor (RAF) scores, national council for prescription drugs (NCPDP) and national provider identifier (NPI) codes, etc.) that may be difficult or impractical for a typical user and/or call agent to decipher.

According to examples provided herein, the computing system can process and translate the health records of the user to generate a dynamic scripting interface for the call agent in connection with a call session with a user. Depending on the current information obtained by the computing system with respect to the user, the computing system can present the dynamic script for the call agent with multiple goals having multiple tiers of priorities. In certain examples, the computing system can execute scripting logic and/or a machine learning model to dynamically respond to information acquired prior to and during a call session in order to dynamically update the scripting interface for the call agent.

As an example, an initial motive of the scripting logic may be to create an emotional connection and/or trust between the call agent and user. Depending on the current information available to the computing system, the scripting logic may identify one or more topics for the user to enable the call agent and user to establish a conversational tone in which the call agent seeks to provide the user with increased satisfaction with regard to the user's health care coverage and/or call agent experience. Such a topic may include, without limitation, the user's personal interests (e.g., as determined from the third-party data), current health issues, family health issues, health history, cost concerns, coverage concerns, and the like. Depending on the available information pertaining to the user (e.g., acquired prior to or during the call session), the scripting logic can prefill the dynamic scripting interface to include, without limitations, known information of the user, such as the user's age, gender, date of birth, age, current health care coverage, home address, work address, occupation, and the like. In doing so, the scripting logic may execute voice-to-text logic for prefilling, or can provide text input boxes in relevant locations on the interface to enable the call agent to manually enter such information.

Once the appropriate permissions are received from the user, the computing system can obtain, process, and translate the coded information of the user's health records in real-time to provide the call agent with prepopulated portions of the dynamic scripting interface (e.g., with plain language summaries of the user's health records), as well as additional scripting for the call agent to progress the call. During this information gathering phase of the call, the scripting logic can progress the dynamic script to enable the computing system to identify specific items related to the individual include, without limitation, any diseases, symptoms, medications, and/or other information about pertaining to the user that may affect the user's choice for a health care coverage plan, any future financial choices, and/or future living choices of the user (e.g., relocating to be closer to family and/or higher quality health care). Further information to be scripted involves identifying the user's allergies, prescriptions, current health care providers, and pharmacies used by the user, including determining whether the user is satisfied with the user's current healthcare arrangement.

During the call session, and as additional information of the user is being gathered throughout the call, the computing system can dynamically score various attributes and benefits of any number of health care coverage plans. Identifying the most optimal plan(s) for a user is a non-trivial undertaking, with current implementations being more reactive to the patient's current health issues, age, gender, and affordability. Furthermore, there exists more than sixty-thousand different health care plans, each providing a unique set of benefits, copays, deductibles, health partnerships, etc. that may be selected by a user or a suggested to the user by a call agent. The result of not providing the patient with the most optimal health care plan that is most tailored to the user's current situation and predicted health outcomes can be increased cost, lack of coverage, poor healthcare access, lower quality care, worse health outcomes, and uncertainty for the user. Furthermore, many people may lack the digital skills required for obtaining health records, translating the records to be readable in plain language, and/or filling out forms in complicated navigation trees to find an optimal health care plan.

Accordingly, while the general state of the health care coverage technology is moving towards more automation and independence for the uninsured or those seeking new insurance coverage to do research and acquire coverage on their own, there is a current need for providing fast and robust assistance to users such that the users have confidence that the assistance process results in the most optimal health care coverage for them on an individual basis. To fulfill this need, the computing system can operate in conjunction with the call agent during a call session to provide dynamic scripting for the call agent based on information pertaining to the user received in real-time, continuously progressing the call session on the front end while simultaneously scoring the various attributes and benefits of health care coverage plans and ranking those plans based on the user's information. This both minimizes the necessary time required for a call session in determining the most optimal coverage plan for the user and eliminates the need for users to log onto a health coverage app or website to enter information and navigate through various screens on their own.

As the call session progresses, the computing system can determine any adverse factors of the user's current prescriptions, including, without limitation, any prescription drugs that may cause significant drug interactions (e.g., rendering other drugs or vaccines less effective and/or causing adverse reactions). In doing so, the computing system can identify prescription equivalents for the user that eliminate or reduce such adverse factors. Upon determining these non-adverse prescriptions, the scripting logic can update the scripting interface so the call agent can provide the user with alternative prescriptions that may improve the user's lifestyle.

The computing system may further predict a set of future healthcare utilizations and health outcomes of the user given the user's current health record and current health trajectory. In some examples, the computing system can process all acquired information pertaining to the user, including, without limitation, survey data concerning individual doctors and health care facilities, health predictions (e.g., future disease, symptoms, treatments, etc.), and user preferences to determine a "circle of care" for the user. A "circle of care" refers to health care coverage that covers the entire current and future needs of the user, based on the user's current health and predicted health outcomes. For example, if the computing system predicts, based on all available information pertaining to the user, that the user should have coverage that encompasses endocrinological care, the scripting logic will provide the call agent with language indicating so to the user, and the computing system will score endocrinological coverage higher in the available health care plans for the user. Furthermore, the computing system can identify gaps in the current health care coverage of the user, and the scripting logic can update the scripting interface to allow the call agent to discuss such gaps with the user. Still further, the computing system, scripting logic, and scoring logic can take into account any preferences of the user, with the scoring logic providing weightings in the stack-rankings of health care plans based on the user's preferences (e.g., when the user indicates that endocrinological coverage is not needed or is less desirable for the user). When the user is amenable to filling those gaps, the call agent can indicate so in the scripting interface, and the computing system can update the scoring and rankings of health care plans accordingly.

In further implementations, the computing system can execute interactive voice recording (IVR) technology that actively monitors the call session for triggers that causes the scripting interface, health outcome and health care utilization predictions (e.g., a probability of future diagnosis or whether the user will require additional medications), and health care plan rankings to be updated, as described in detail below. In utilizing IVR, the computing system can detect when a user provides permission to obtain health records from any number of health record databases (e.g., detecting a voiced affirmation or when the user provides a required input on the user's phone). The computing system can further monitor the call session for emotional responses and answers from the user to the call agent's questions to update the dynamic script and health plan rankings.

It is contemplated that the computing system's convergence on a most optimal health care plan for the user will seek to maximize the individually tailored coverage for the user (e.g., based on the user's budget, current state of health, predicted health outcomes, etc.) while minimizing the cost of such coverage. It is further contemplated that preventative care using such individually optimized plans can result in significantly reduced overall costs across a population.

In one example, a call session may be initiated by a call agent with a user who has taken a cognitive assessment test with the computing system. During the call, a scripting interface is presented on a computing device of the call agent, who may perform the call over a network link on the computing device or on a typical telephone (e.g., a landline or cellular phone). The scripting logic can process currently obtained information of the user (e.g., name, age, gender, weight, height, home address, etc.) to update the scripting interface to establish a conversational tone (e.g., an emotional or identifiable connection) with the user. If the computing system has not received authorization to access the user's health records, the scripting logic can update the dynamic script to ask for such permissions and any necessary login information, access codes, links, passwords, etc. In one example, the user can link the user's access to various health system databases via a website or user application provided by the computing system.

While the call progresses, the computing system can utilize the user's permissions to access the user's health records from the health system databases in real-time, and provide analysis including, without limitations, translating the coded records (e.g., CPT and ICD codes for determining the user's prescriptions and diagnoses), and updating the scoring of health care plan benefits and health care plan rankings. The computing system can further identify the user's current prescription medications, past and current treatment plans, diagnoses, current health care providers, past medical procedures (e.g., surgeries), and the like. Concurrently, the scripting logic can proceed with determining whether the user is planning to move, where the user's family is located (e.g., in case the user will need support), any current symptoms the user is experiencing, any exercise routines of the user, and any other relevant information for ultimately determining an optimal health care coverage plan for the user. The computing system can further process this dynamically acquired information to identify any coverage gaps (e.g., unnecessary or overly expensive copays, out-of-scope prescriptions, probable future coverage needs) in the user's current health care coverage. The scripting logic can enable the call agent to discuss such gaps with the user and determine whether the user wishes to close the gaps in coverage.

The call agent can provide inputs on the scripting interface indicating the user's answers, which the computing system processes in real-time to update the health plan scoring and rankings. In some examples, the computing system can identify where the user is excelling in health for the user's age and/or gender (e.g., a low number of prescriptions, good BMI, good blood pressure, overall health, etc.) and the scripting logic can provide celebratory scripting for the call agent, such that the user is provided with positive feedback regarding the user's good health and/or health habits. In certain implementations, the computing system can monitor the call for any abnormalities or emotive responses to provide further scripting for the call agent. The user is further able to decline certain coverages for any reason (e.g., the user is on a diet or nutrition plan, or due to increased cost), and the computing system updates the scoring and rankings of health plans accordingly.

In still further implementations, the computing system can process the user's health records and any information provided by the user and/or call agent to determine a "digital skill" level for the user, or how savvy the user may be in operating computing devices, apps, websites, using video conferencing, receiving and responding to electronic messages, and the like. This digital skill level may be utilized by the computing system in filtering through health care coverage plans that are more geared towards telehealth visits or checkups over a computer versus in-person visits. At any given time during the call session, the computing system can determine an optimal health care plan for the user, and the scripting logic can intervene to instruct the call agent to propose the plan for the user. It is contemplated that the more information received regarding the user, the more precise the computing system can converge on an optimal health care plan for the user. However, certain overarching concerns can cause a particular health care plan to be ranked highest (e.g., robust coverage for a certain type of cancer), which can result in time savings for both the user and call agent. The scripting logic can indicate that no further information is needed and that a most optimal plan has been found for the user.

For certain users in the United States, the computing system can further filter health care coverage plans to include or prioritize Medicare plans, as well as certain types of auto insurance and/or life insurance plans. Furthermore, if the user has provided survey information regarding a particular health care plan, one or more doctors, and/or one or more health care facilities, the computing system can determine a set of preferences for the user, and update the health plan scoring and rankings accordingly.

According to additional examples described herein, a computing system can execute a customer relations management system to implement dynamic assistance for users of a health service. A call agent can initiate a call session with a user, who can provide certain information for processing by the computing system. For example, the user may provide an authorization (e.g., during a call session or via input on a website or application interface prior to or during the call session) to enable the computing system to obtain the user's health records from any number of health care sources. These health records can include, without limitation, the user's history of health care visits, diagnoses, treatments, prescriptions, test results, insurance claims, and other health-related information. In some examples, the user can set up an account with the computing system and provide credential information, such as, but not limited to, a username or a phone number with a link, code, or password. Additionally or alternatively, the user can provide any permissions and/or credentials prior to or during a call session with the call agent. Using the credential information, the computing system can access health record information from a plurality of health record systems, such as, but not limited to, hospital appointment and/or visit records, diagnosis information, treatment information, prescription information, past health procedures (e.g., surgeries, screening, tests, etc.), and the like.

In various examples, the computing system can automatically process and translate the health records of the user to generate a live agent interface for the call agent in connection with a call session with a user. Depending on the current information obtained by the computing system with respect to the user, the computing system can present the live agent interface on a computing of the call agent, which can dynamically update based on inputs provided by the call agent during the call session with the user. The live agent interface can comprise a set of input features that enables the call agent to provide inputs based on information provided by the user during the call session. As provided herein, the real-time inputs provided by the call agent can comprising input data for a health plan ranking engine, which can execute one or more optimization techniques to output a personalized ranking of health care plans for the user.

As provided herein, a "call session" can comprise any interactive session between the call agent and the user, which can include telephonic communications, text messaging, email, live application-based messaging, video conferencing, and any combination of the foregoing. For example, a call session can comprise a telephonic call from a call agent to a user in combination with an interactive user interface being presented to the call agent on a computing device. As the call session progresses and more information is provided by the user, a backend computing system can process the additional information and dynamically generate a personalized health plan ranking for the user.

Once the appropriate permissions are received from the user, the computing system can obtain, process, and translate the coded information of the user's health records in real-time to provide the call agent with an interactive agent interface that enables the call agent to input filters for the ranking of health plans. For example, the interactive interface can ensure that crucial information regarding the user's preferred doctors, pharmacies and necessary prescriptions, and current and predicted diagnoses are inputted into the interactive agent interface, such that the computing system can accurately optimize a ranking of health care plans for the user.

During the call session, and as additional information of the user is being gathered throughout the call, the computing system can dynamically score various attributes and benefits of any number of health care coverage plans. As described herein, the computing system operates in conjunction with the call agent during a call session to provide the interactive agent interface that supports the progression of the call session while scoring the various attributes and benefits of health care coverage plans and ranking those plans based on the user's information. As the call session progresses, the computing system can automatically determine any adverse factors of the user's current prescriptions, including, without limitation, any prescription drugs that may cause significant drug interactions. In doing so, the computing system can identify prescription equivalents for the user that eliminate or reduce such adverse factors. Upon determining these non-adverse prescriptions, the scripting logic can update the scripting interface so the call agent can provide the user with alternative prescriptions that may improve the user's lifestyle.

Furthermore, the computing system can identify gaps in the current health care coverage of the user, and the health care plan rankings can allow the call agent to discuss such gaps with the user and discuss or otherwise provide information to the user concerning plans that fill such gaps. Still further, the interactive agent interface can provide interactive features corresponding to any preferences of the user, with the scoring logic providing weightings in the stack-rankings of health care plans based on the user's preferences (e.g., when the user indicates that endocrinological coverage is not needed or is less desirable for the user). When the user is amenable to filling those gaps, the call agent can indicate so in the interactive interface, and the computing system can update the scoring and rankings of health care plans accordingly.

In an example, a call session may be initiated by a call agent with a user. During the call, an interactive agent interface is presented on a computing device of the call agent, who may perform the call over a network link on the computing device or on a typical telephone (e.g., a landline or cellular phone). The call agent can reference the interactive interface to ask questions to the user (e.g., asking for the user's required or preferred doctors, prescriptions and/or pharmacies, and current diagnoses), process currently obtained information of the user (e.g., name, age, gender, weight, height, home address, etc.) to update the individualized health care plan rankings for the user.

During the call session, the call agent can provide inputs on the interactive interface indicating the user's answers, which the computing system processes in real-time to update the health plan scoring and rankings. In some examples, the computing system can identify where the user is excelling in health for the user's age and/or gender (e.g., a low number of prescriptions, good BMI, good blood pressure, overall health, etc.) and provide such information to the call agent via the interactive agent interface, such that the user is provided with positive feedback regarding the user's good health and/or health habits. The user is further able to decline certain coverages for any reason (e.g., the user is on a diet or nutrition plan, or due to increased cost), and the computing system updates the scoring and rankings of health plans accordingly. In further implementations, the interactive agent interface can present the call agent with a side-by-side comparison of the user's current plan and each ranked health care plan as ranked by the computing system.

At any given time during the call session, the computing system can determine an optimal health care plan or optimal health care plan ranking for the user, and the interactive agent interface can be updated to allow the call agent to present the optima plan or plan rankings for the user. It is contemplated that the more information received regarding the user, the more precise the computing system can converge on an optimal health care plan for the user. For Medicare users in the United States, the computing system can further filter health care coverage plans to include or prioritize Medicare plans, as well as certain types of auto insurance and/or life insurance plans. Furthermore, if the user has provided the call agent with information regarding a particular health care plan, one or more doctors, and/or one or more health care facilities, the computing system can determine a set of preferences for the user, and update the health plan scoring and rankings accordingly.

In further examples, a call session between a call agent and a user is not required to perform the health outcome prediction and health plan ranking techniques described throughout the present disclosure. In such examples, a web portal or application interface is provided directly to the user computing devices that enables the users themselves to navigate and provide the necessary authorization(s) and information that trigger the computing system to obtain the user's health records and perform the health prediction and health plan ranking processes described herein.

As used herein, a computing device refers to devices corresponding to desktop computers, cellular devices or smartphones, personal digital assistants (PDAs), laptop computers, virtual reality (VR) or augmented reality (AR) headsets, tablet devices, television (IP Television), etc., that can provide network connectivity and processing resources for communicating with the system over a network. A computing device can also correspond to custom hardware, in-vehicle devices, or on-board computers, etc. The computing device can also operate a designated application configured to communicate with the network service.

One or more examples described herein provide that methods, techniques, and actions performed by a computing device are performed programmatically, or as a computer-implemented method. Programmatically, as used herein, means through the use of code or computer-executable instructions, and includes the implementation of machine learning and/or artificial intelligence to execute the processes described throughout the present disclosure. These instructions can be stored in one or more memory resources of the computing device. A programmatically performed step may or may not be automatic.

One or more examples described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs, or machines.

Some examples described herein can generally require the use of computing devices, including processing and memory resources. For example, one or more examples described herein may be implemented, in whole or in part, on computing devices such as local or remote servers (e.g., cloud computing infrastructure), desktop computers, cellular or smartphones, personal digital assistants (e.g., PDAs), smartwatches, wearable and other remote patient monitoring technologies (e.g., activity monitoring devices), laptop computers, VR or AR devices, printers, digital picture frames, network equipment (e.g., routers) and tablet devices. Memory, processing, and network resources may all be used in connection with the establishment, use, or performance of any example described herein (including with the performance of any method or with the implementation of any system).

Furthermore, one or more examples described herein may be implemented through the use of instructions that are executable by one or more processors. These instructions may be carried on a computer-readable medium. Machines shown or described with figures below provide examples of processing resources and computer-readable mediums on which instructions for implementing examples disclosed herein can be carried and/or executed. In particular, the numerous machines shown with examples of the invention include processors and various forms of memory for holding data and instructions. Examples of computer-readable mediums include permanent memory storage devices, such as hard drives on personal computers or servers. Other examples of computer storage mediums include portable storage units, such as CD or DVD units, flash memory (such as carried on smartphones, multifunctional devices or tablets), and magnetic memory. Computers, terminals, network enabled devices (e.g., mobile devices, such as cell phones) are all examples of machines and devices that utilize processors, memory, and instructions stored on computer-readable mediums. Additionally, examples may be implemented in the form of computer-programs, or a computer usable carrier medium capable of carrying such a program.

System Description

FIG. 1 illustrates computing system 100 implementing health prediction and planning service for users, in accordance with examples described herein. The computing system 100 can include a communication interface 105 that connects the computing system 100, over one or more networks 160, with health record systems 190 and computing devices 170 of users 175. In certain examples, the computing devices 170 can include smartphones, personal computers, etc., and can execute a designated application 172 that provides a network connection to the computing system 100.

In various implementations, the users 175 can set up accounts with the computing system 100 and authorize the computing system 100 to access health records of the users from the health record systems 190. As provided herein, the health record systems 190 can comprise computing systems and databases of health care providers, insurance providers, and the like. The computing system 100 can include a record compiler 120 that transmits record requests to the health record systems 190 (e.g., using credential information from the user 175). In certain examples, the user 175 can provide unique credential information, such as personal information (e.g., name, age, address, etc.), and usernames and passwords (and/or other access information) for each of the user's health institutions (e.g., to enable the record compiler 120 to obtain the user's health records from each institution). Upon providing the credential information, the record compiler 120 can access and obtain the health record systems 190 of the health care institutions and/or health insurance companies of the user 175. Such health records can be disputed by the user 175 and can correspond to insurance claims, insurer records, doctor records and/or notes, and the like. In various implementations, the record compiler 120 can periodically poll the health record systems 190 for any updated information pertinent to the user 175.

In some aspects, the computing system 100 can include a database 115 including a user profile 116 for each user 175, which can include the user's personal information and the entirety of the user's health record information. As described in detail below the user profile 116 of a particular user 175 may be updated as new health records are obtained and/or when a health record verification process confirms the user's health records as accurate and complete. The database 115 can further include historical data 117 that indicates various correlations between health conditions, health risks, treatments, prescriptions, diagnoses, health risks, lifestyles, nutrition and diet, location of residence, demographic information, longevity, and the like. The historical data 117 can further include health research data indicating adverse impacts between prescribed medications, treatments, procedures, and the like.

The database 115 can further include health care provider data 118 indicating doctor quality and/or effectiveness (e.g., based on survey data and/or patient outcomes), health care institution quality (e.g., for particular treatments and/or diagnoses), health care facility locations and quality, and cost information. In further examples, the provider data 118 can further include survey data for health care providers, individual doctors, health insurance providers, etc. to provide understanding of any social determinant barriers to adequate healthcare. The survey data may be collected from third-party resources, such as medical journals and/or public health resources, and/or may be collected through surveying the users 175 themselves.

In further examples, the record compiler 120 can provide surveys to the users 175, which can prompt the users 175 to provide personal contextual information regarding their health care providers, insurers, physicians, etc. In various implementations, the survey data provided by the individual users 175 can enable the health planning engine 145 to more specifically tailor recommendations for risk mitigation plans and health care providers, and may further be utilized to determine ratings for health care providers, insurers, etc. In further implementations, a user 175 can input their review of a doctor, drug, and/or service based on the quality of care they received, which can be processed by the health planning engine 145 to provide health plan recommendations. Still further, the user 175 may be permitted to find a new doctor based on a recommended or requested course of care. The user 175 may also be enabled to identify other courses of care, service, or drugs to discuss with their doctor based on the experiences of other patients.

In various examples, the computing system 100 can include a health record parser 140 that receives and parses the health record data from the record compiler 120. In parsing the health record data for a particular user 175, the health record parser 140 can execute code translation logic that translates the various nomenclature and code information in which the health records are stored into plain language information. For example, the health records of the user 175 may include information relating to procedures performed on the user 175, diagnosis and disease information, disability information, prescription information, which may be stored as current procedure terminology (CPT) codes, health common procedure coding system (HCPCS) codes, internal classification of diseases (ICD) codes, internal classification of functioning, disability, and health (ICF) codes, diagnostic-related group (DRG) codes, national drug codes (NDC codes), code on dental procedures and nomenclature (CDT), diagnostic and statistical manual of mental disorder (DSM) codes, hierarchical condition category (HCC) scores, risk adjustment factor (RAF) scores, national council for prescription drugs (NCPDP) and national provider identifier (NPI) codes, NCS numbers, doctor's notes, lab data, images, self-assessments by patients, genetic information, notes and treatment plans from nursing homes, health-knowledge quiz results, etc. Genetic information can be determined from a genetic test (e.g., such as may be determined from genetic testing, if ordered by a doctor or provided by a user), and/or inferred based on health information provided by the user about his family (e.g., parents, siblings, etc.). Genetic testing can include commercial tests, as well as specific tests that link an individual to a particular medical condition. Genetic information can further reflect predispositions or probabilities. For example, the genetic information can reflect a determination that a user has a genetic predisposition towards a medical condition based on a parent of the user having the same medical condition. Some health information about the user may be provided through manual input, such as by the user. Some information, such as doctor notes, can also be subject to optical character recognition ("OCR"). The health record parser 140 can execute translation logic that translates these codes into plain language definitions or descriptors.

As provided herein, the health records of a user 175 can include prescriptions, doctors, and health-related conditions of the user 175, as well as the electronic health records of the user 175. The health records can further include health claims of the user 175. The health records can further include doctor's notes pertaining to the user 175, which can be automatically converted by the health record parser 140.

When the user's health records have been parsed and translated, the health record parser 140 can initiate a verification process with the user 175 to enable the user to confirm or dispute each health record. For example, the health record parser 140 can generate content data that causes the computing device 170 of the user 175 to present an individualized user interface that includes content comprising the plain language translations of each health record. As provided herein, the user interface can include confirmation requests for each of the user's health diagnoses, treatments, health care facility visits, prescriptions, and other health-related information pertaining to the user 175.

In certain scenarios, the user 175 may be unable to recall information corresponding to a particular health record. For example, the user interface may present a content screen or panel requesting the user 175 to confirm a particular prescription that the user 175 does not recall being prescribed. As such, the content screen or panel can include a selectable feature (e.g., stating "I don't recall") that triggers the health record parser 140 to provide additional contextual information related to the health record. In the case of a forgotten or mistakenly prescribed prescription, the health record parser 140 can cause one or more images related to the drug to be presented to the user 175, such as an image of a pill, a recognizable brand name equivalent of the pill, a description of which health issue the drug is prescribed to treat, and the like.

In attempting to stimulate the user's memory, the health record parser 140 can further provide additional contextual information to the user 175, such as an original date at which the drug was prescribed, a location and/or doctor that prescribed the drug, and image of the health care facility (e.g., an outdoor entrance façade) at which the drug was prescribed, a name of the health care facility at which the drug was prescribed, and the like. In some examples, the user's memory may be successfully stimulated by the additional contextual information, and the user 175 may confirm the health record or amend or dispute the health record. For example, if the user 175 is no longer taking the prescription, the user 175 may request that the health record be amended to indicate that the prescription has been canceled.

It is contemplated that the memory stimulation techniques may be performed for the user 175 for any particular health record, such as records indicating diagnoses, treatments, hospital visits, etc. The user 175 may confirm the health record, refute the health record, or indicate a lack of memory or contextual information. In certain examples, the health record parser 140 can identify any anomalous health records that do not appear consistent with other health records, such as an anomalous procedure or prescription that does not appear to relate to the user's diagnoses and treatments. Such anomalous health records may be flagged for the user 175 for verification with a contextual alert indicating the anomaly.

When the user 175 is confident that a health record is incorrect or should not exist, a dispute module 130 of the computing system 100 can initiate a dispute process for the user 175. A user interaction with the individualized user interface may indicate trigger the dispute module 130 to record or indicate the disputed health record in the user's profile 116, and generate a dispute query to be transmitted to the relevant health record system 190 storing the disputed health record. In some aspects, the dispute module 130 acts as an assistant for the user 175, providing links to forms or documents needed for the user 175 to pursue the dispute, as well as instructions corresponding to which entity to contact and submit the forms and documents. In alternative aspects, the dispute module 130 can act as a facilitator and perform auto-filling techniques for any particular form or document needed to dispute a health record. For example, the dispute module 130 can prefill any boxes or form sections with known information stored in the user's profile 116, and can present a series of user interface features that query the user 175 for any necessary information that cannot be prefilled and automatically complete the form or document accordingly. In further examples, the dispute module 130 can also automatically transmit the necessary dispute documents to the relevant health record system 190 or claims vendor to facilitate in resolving the dispute.

In further implementations, the health record parser 140 enables the user 175 to readily update a list of medications prescribed to the user 175. For example, the user 175 can remove stray medications that the user 175 no longer uses or has replaced with another medication from a different health care provider. On the backend, the health record parser 140 may automatically update the user's health care providers with any changes to the user's medication list.

It is contemplated that medical record defects or health care fraud can result in significant risks to patients, both physical and financial. For example, a fraudulent health record may be the result of identity theft and can involve prescription drugs being sent to the wrong person under the guise of an unknowing user 175. Accordingly, the health record parser 140 and dispute module 130 facilitate in identifying any potential health records that are incorrect or fraudulent, and can further provide pathways to finding the sources or perpetrators of such incorrect or fraudulent information. In implementing the health record verification and dispute processes, the health record parser 140 and dispute module 130 can create a more robust health record for the users 175 such that subsequent health services can be more individually tailored for the users 175.

Once such health service can comprise health prediction, which can process the user's verified health records using the historical data 117 and provider data 118 to generate a health risk profile for the user 175. The computing system 100 can include a health outcome prediction engine 135 that utilizes the various correlations in the historical data 117 and provider data 118 to generate the health risk profile for the user 175 based on the user's verified health records. For example, given the user's health records—indicating the user's current personal information (e.g., weight, age, height, ethnicity, gender or sex, demographics, location or residence, lifestyle, diet, etc.) as well as the user's current health care information (e.g., current diagnoses, treatments, prescriptions, previous screenings and medical and/or surgical procedures, health care provider(s), doctor(s), etc.)—the health outcome prediction engine 135 can identify a set of correlations with known patients having similar personal and health information. Further, health outcome prediction engine 135 can determine predispositions (or probabilities) of the user towards having or not having a particular medical condition based on genetic information determined or obtained about the user.

In examples, a user's health risk profile 175 can also include an inference of a user's medical condition based on current or past diagnosis or prescriptions. In such examples, the inference may be probabilistic (e.g., likely, highly probable, etc.), to identify a medical condition that is not explicitly stated in the user's medical records. Further, based on the user's health profile 175, the user's health profile can also make assumptions about the user's life-style (e.g., user does not exercise). The health outcome prediction engine 135 can also implement steps to confirm inferences, such as by generating questions for the user to confirm regarding the determined inferences.

In various implementations, the historical data 117 can comprise ground truth information indicating the medical outcomes of patients that had similar health records and personal information as the user 175. Thus, the health outcome prediction engine 135 can perform health record matching techniques to identify a set of probable health outcomes, health risks, life expectancy, and mortality risk for the user 175 based on the user's current information. In doing so, the health outcome prediction engine 135 can generate and provide a set of health predictions for the user 175, such as a mortality table indicating probability of death within a certain timeframe and a set of health risks for particular diseases (e.g., various types of cancer, heart disease, gastrointestinal disease, diabetes, respiratory diseases, Alzheimer's disease, etc.). For example, based on the user's current health record information, the historical data 117, and the provider data 118 of the user 175 (e.g., the user's current doctor(s) and health care provider(s)), the health outcome prediction engine 135 can output a prediction that the user 175 is at risk of diabetes, heart disease, heart attack, and prostate cancer within the next three years.

In further implementations, the health outcome prediction engine 135 can generate a quantitative risk prediction for the user 175 based on the user's health records, such as a percentage risk of a medical problem, acute health emergency, or chronic condition over a future period of time. The health outcome prediction engine 135 can further provide the user 175 with additional information, such as the average risks of these medical issues for people with similar attributes of the user 175 (e.g., similar age, weight, height, sex, etc.), as well as the average risks for other populations of users. In some aspects, the health outcome predication engine 135 can further generate, based on the user's health records and other information provided, a probability of the user 175 requiring a particular medical procedure (e.g., surgery, treatment programs, etc.). The health outcome prediction engine 135 can further provide the user 175 with average medical procedure probabilities for people with similar attributes to those of the user 175.

In further implementations, the health outcome prediction engine 135 can further process the verified health records of the user 175 to determine any adverse factors in which any of the user's current prescription medications, treatments, over-the-counter drugs and supplements, and health risks or current health issues may adversely impact other current prescription medications, treatments, and health risks or current health issues of the user 175. As an example, the user 175 may have medications prescribed from two different health care providers that may cause adverse reactions, side effects, or otherwise increase health risks to the user 175. As another example, a current treatment for a chronic illness experienced by the user 175 may exacerbate another health issue of the user 175. For each detected adverse factor, the health outcome prediction engine 135 can provide a notification or alert to the user 175, which the user 175 can utilize to have a discussion with the user's health care providers and potentially alter a treatment or prescription accordingly and eliminate the adverse factor. In further examples, the health outcome prediction engine 135 can identify any prescribed medications or over-the-counter medications or supplements that are potentially unsafe for the user 175 (e.g., based on the user's age).

It is contemplated that active user engagement with accurate health outcome predictions provides critical awareness for the user's in reducing or mitigating health risks and promoting longer, healthier lives. In various implementations, the computing system 100 can include a health planning engine 145 that can utilize the generated predictions, profile data of the user 175, and/or provider data 118 to interact with the user 175 in planning physically and financially for medical procedures and treatments, selecting optimal health care providers and/or individual doctors based on the health outcome predictions, providing highly tailored health-related literature for the user 175 (e.g., updated newsletters pertaining to the user's current health issues and risks), and providing health risk mitigation and prevention services for the user 175. The computer system 100 can, for example, include or access a collection of content items, including journals (or summaries), wellness articles and other content items, where such content items are categorized to medical conditions or attributes of users. In some variations, the categorizations can be programmatically determined using, for example, key words, semantic classifiers, and/or language processing. Further, the computing system can include processes to compile and/or such publications into an individualized newsletter (or content aggregation) for the user. As an addition or alternative, the personalized content aggregation can encompass topics such as financially planning and social outreach (e.g., social platforms) that are specific to medical conditions or other attributes (e.g., good health) of individual users.

In certain examples, the newsletter may include features that prompt the user 175 for input regarding the user's health experience with a particular health care provider. The user's input information may be shared with insurers so, for example, current insurers can identify users 175 seeking assistance to provide those users 175 with modified or additional preventative care before complications occur (e.g., disease progression that requires lengthy hospital stays). In further example, the newsletter prompts may also affect an insurer's rating (e.g., Medicare star rating), and can incentivize insurers to identify substandard care and, for example, move resources to certain users 175 before formal rating surveys are sent, which other insurers can access and target users 175 that are having negative experiences with their current insurance plans. In some aspects, the newsletter may also introduce a gamification system (e.g., including monetary and non-monetary rewards, score system, leaderboard, etc.) to incentivize users 175 to engage with the individualized health education content and surveys described herein.

In an initial planning phase, the health planning engine 145 can process the user's verified health records to identify the current health risks and predicted health outcomes facing the user 175. Based on this information, the health planning engine 145 can present a set of recommended risk mitigation plans for the user 175, which can include recommended health insurance plans, life insurance plans, automobile insurance plans, etc. The recommended risk mitigation plans can comprise plans that provide maximum care for the user 175 based on affordability for the user 175, which may be actively queried or inferred based on the user's personal information. In various examples, the health planning engine 145 can further utilize the historical data 117 to accurately predict the future costs of health care for the user for anticipated screenings, treatments, medications, and procedures, etc. In such examples, the health planning engine 145 can generate content data that causes the user interface presented on the user's computing device 170 to indicate the predicted costs and potential areas of savings in the user's health records, and enable the user 175 to plan financially for future medical expenses.

In one example, the health planning engine 145 can identify less costly drug equivalents for the user's prescription medications that would not adversely affect the user 175. In further examples, the health planning engine 145 can provide a recommended health care plan (e.g., a health insurance plan) or health care provider for the user 175 that would result in lower costs with minimal impact to health care quality. Conversely, the health planning engine 145 may determine that the user 175 may be able to afford a more expensive, higher quality health care plan that may provide added health treatment benefits than lower cost plans. In providing plan recommendations, the health planning engine 145 may query the user 175 for personal financial information, expenditures, liabilities, income, assets, etc. to determine an affordability factor for the user 175 in order to make more robust health recommendations.

The health planning engine 145 can further process the user's profile data to determine one or more health care preferences of the user 175, such as the particular qualities in a doctor or health care that the user 175 highly values (e.g., bedside manner, cost, popularity, etc.). Based on the user's insurance coverage, health issues and risks, and preferences, the health planning engine 145 can determine an optimal health care provider and individual doctor for the user 175 and provide the user 175 with information indicating the match. As an example, a user 175 with diabetes may prefer a doctor that is rated highly by other patients and that provides exceptional care for patients with diabetes. The health planning engine 145 can parse through the provider data 118 to identify an optimal doctor that matches the user's preferences and specializes in diabetes care.

In various implementations, the health planning engine 145 can engage with the user 175 through one or more health planning sessions to provide customized lifestyle recommendations that would mitigate or reduce the current and predicted health risks of the user 175. For example, the health planning engine 145 may determine that the user 175 will require physical assistance in the near future, and recommend that the user 175 relocate to an area or residence where family or friends may provide the necessary assistance. In a further example, the health planning engine 145 can provide more granular lifestyle recommendations, such as dietary recommendations (e.g., eliminating certain foods from the diet), exercise recommendations (e.g., taking a thirty minute walk every morning and evening), stress reduction recommendations (e.g., starting a mentally relaxing hobby, such as gardening, cooking, or playing a musical instrument), and the like.

According to some examples, the health planning engine 145 can further provide the user 175 with customized health knowledge based on the user's health record information to promote lifestyle changes that reduce the user's health risks. The health planning engine 145 can further act as a health assistant to the user 175, providing notifications via the designated application 172 for recommended routines, medication adherence, scheduled medical appointments, and the like. As such, the health assistance services provided by the health planning engine 145 can integrate the user's verified health record information into the health assistance service such that the recommendations provided to the user 175 are more individually tailored to meet specific health goals that current implementations.

In certain implementations, the health planning engine 145 can provide the user 175 with a health consciousness score or general health score that continually updates based on the user's interactions with the health planning engine 145, updates to the user's health records (e.g., a recent visit indicating improved vitals, such as blood pressure, blood test results, cholesterol levels, gut health, cognitive test results, and the like), risk adjustment factor (RAF), and the user's diagnoses and or ICD codes. The health consciousness score or general health score can be based on the user's current health status as indicated in the user's health records as well as the user's diligence in seeking preventative care. In some aspects, the health consciousness score and/or general health score can be adjusted based on the user's age, sex, and other attributes and/or factors.

Methodology

Figure 2:
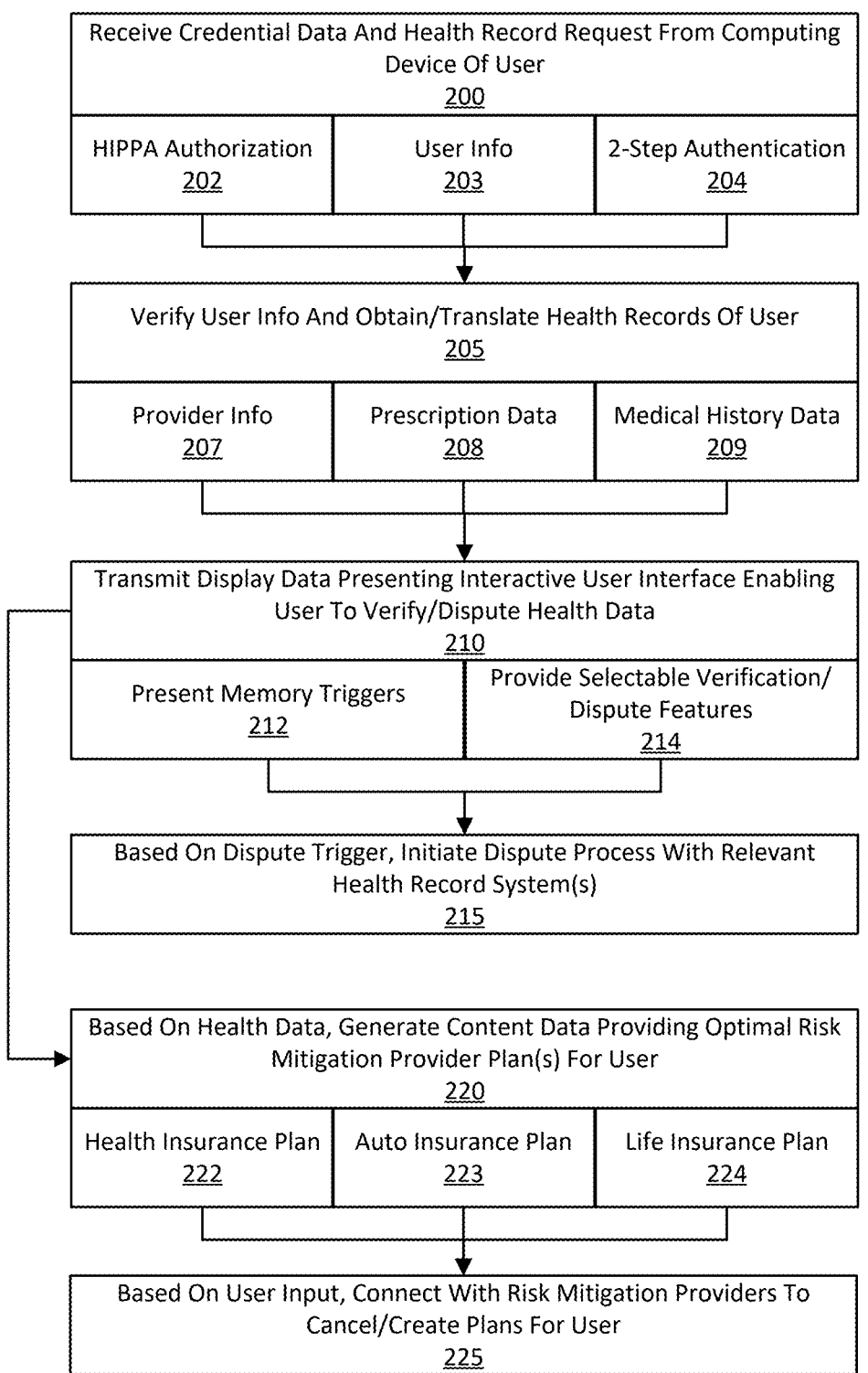
FIG. 2 is a flow chart describing a method of providing a health history compilation, dispute, and risk mitigation planning service, according to various examples.
Figure 3:
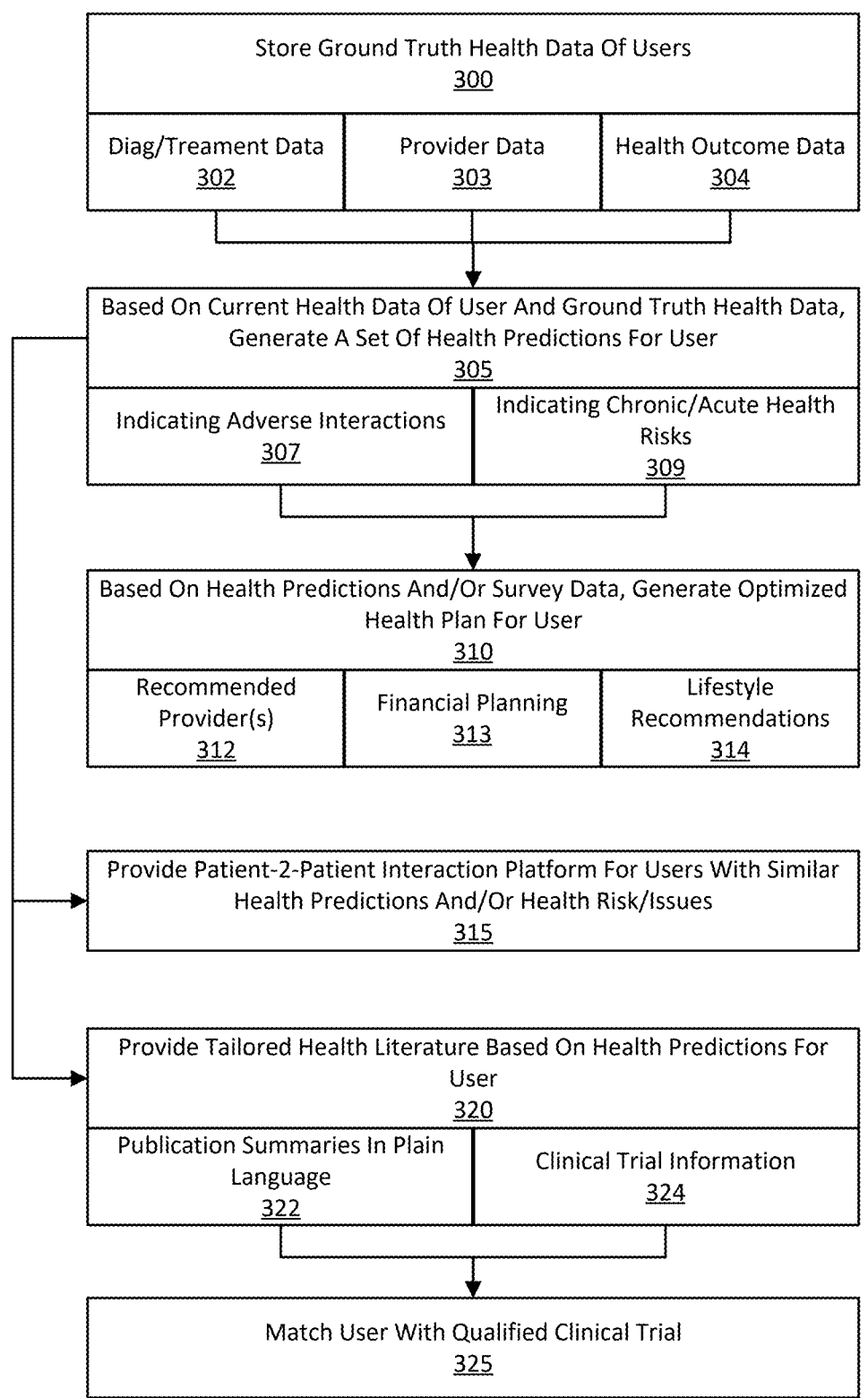
FIG. 3 is a flow chart describing a method of utilizing health record data to tailor health-related services for users, according to various examples.

FIGS. 2 and 3 are flow charts describing a method of providing a health history compilation, dispute, and risk mitigation planning service, and a method of utilizing health record data to tailor health-related services for users, according to various examples. In the below discussion of FIG. 2, reference may be made to reference characters corresponding to like features as shown and described with respect to FIG. 1. Furthermore, the steps described in connection with FIG. 2 need not be performed in any particular order, and any step described may be precede or may be performed subsequent to any other step. Referring to FIG. 2, the computing system 100 may receive credential data and a health record request from a computing device 170 of a user (200). As described herein, the credential data can include a HIPAA authorization (202) and personal user information, such as usernames, passwords, access information, etc. to access the user's health records from various health record databases (203). The personal information can be utilized by the computing system 100 to access the health system databases and obtain a corpus of the user's health records over a given time period (e.g., the previous two years). In certain examples, the computing system 100 can provide a two-step authentication feature for additional security (204).

According to examples provided herein, the computing system 100 can verify the user's credential information and obtain and translate the health records of the user 175 (205). In various implementations, the health records can comprise the user's health care provider information (e.g., the user's doctors, health insurance, current health insurance plan, visited medical facilities, etc.) (207). The health records can further comprise the user's prescription data indicating which prior and current prescription drugs the user 175 has been prescribed (208). The health records can further comprise the user's medical history data, including health care facility visits, diagnoses, treatments, procedures (e.g., screenings, surgeries, etc.), and the like (209). As described above, the health records may be stored in coded format using a number of health code protocols. The computing system 100 can be programmed or can execute code translation logic to convert the health records into plain language.

In various examples, the computing system 100 can initiation a health record verification and dispute process by transmitting display data to the computing device 170 of the user 175, where the display data causes the computing device 170 to present an interactive user interface enabling the user to verify and/or dispute health records (210). In instances in which the user 175 is unable to remember a particular health record, the computing system 100 may cause the interactive user interface to present memory triggers, such as images and contextual information corresponding to the health record, as described above (212). The interactive user interface can provide selection features that enable the user 175 to verify or dispute a particular health record (214).

Based on a dispute trigger for a particular health record, the computing system 100 can initiate a dispute process with the relevant health record system(s) (215). In doing so, the computing system 100 can facilitate in provide the necessary documents and/or links that enable the user 175 to submit a dispute request. In variations, the user 175 is enabled to perform the dispute process through the interactive user interface, while the computing system 100 executes automated form filling and submission techniques for the user 175. In implementing the verification and dispute processes for the user 175, the computing system 100 facilitates in compiling a robust and accurate medical history for the user 175.

Based on the user's health record data, the computing system 100 can generate content data providing optimal risk mitigation plans for the user 175 (220), such as health insurance plans (222), life insurance plans (224), and automobile insurance plans (223). The optimal risk mitigation plans can be determined based on the user's current medical diagnoses and treatment needs, cost, and locale. In various implementations, based on user input on the interactive user interface, the computing system 100 can connect with risk mitigation providers to create and/or cancel risk mitigation plans for the user 175 (225).

Referring to FIG. 3, the computing system 100 can store ground truth health data of a user base (300). The ground truth health data can comprise screening, diagnosis, treatment, and procedure information for each of the users 175 (302). The ground truth health data can further comprise health care provider data, indicating which health care providers each user 175 utilizes for health care (303). The ground truth health data can further include health outcome data, indicating whether the user 175 recovered from a particular diagnosis and treatment, the nature of the recovery, side-effects, lasting impacts on the user's livelihood, how long the recovery took, mortality information, and the like (304). The ground truth health data also includes personal information, such as each user's age, weight, height, gender or sex, demographic information (e.g., income, residence, genetic background, etc.). As such, each user 175 or a subset of the users 175 for which a health records exist and health outcomes are known, can comprise a control group that enables the computing system 100 to predict health outcomes of a present user based on the ground truth health data.

In various implementations, the computing system 100 can generate a set of health outcome predictions for the user 175 based on the user's verified health record data and the ground truth health data (305). The health outcome predictions can indicate any adverse interactions between medications, treatments, current health issues and risks, and over-the-counter supplements and drugs (307). The health outcome predictions can further indicate any chronic or acute health risks facing the user 175 over a given time frame (e.g., the next five years) (309). In further examples, the computing system 100 can provide the user with a set of recommendations, such as foods and/or activities to avoid, or foods and/or activities to consume and perform (e.g., healthy foods, exercise routines).

Based on the health outcome predictions, user preferences, and/or survey data, the computing system 100 can generate an optimized health plan for the user 175 (310). The optimized health plan can include recommended health care providers that are highly rated and/or meet the preferences of the user 175 (e.g., doctors specializing in treating an ailment suffered by the user 175) (312). The optimized health plan can also include a financial plan based on a set of estimated costs the user 175 is expected to pay for medical expenses over a given time frame (313). The optimized health plan can further include lifestyle recommendations based on current research that would prevent or reduce health risks associated with the health outcome predictions for the user 175 (314).

In various examples, the computing system 100 can further provide a patient-to-patient interaction platform that enables the user 175 to connect and interact with other users 175 having similar health issues, risks, or outcome predictions (315). It is contemplated that social interaction between like users 175 can result in increased motivation to pursue preventative and mitigative health behaviors that can increase health wellness and longevity. In certain examples, the computing system 100 can further provide individually tailored health literature based on the health outcome predictions of the user 175 (320). Such health literature is often technical in nature, using medical terminology that may not be readily decipherable by a typical user 175. Accordingly, the computing system 100 can parse the literature (e.g., research journals and clinical trial results) to provide plain language summaries of such publications (322).

In certain examples, the targeted health literature for the user 175 may include clinical trial information that is pertinent to the user 175 based on the user's 175 medical records (324). In such examples, the computing system 100 may determine that the user 175 qualifies as a candidate for a particular clinical trial, and can match the user 175 with the clinical trial (325). For example, the computing system 100 can provide contact information for the clinical trial and facilitate communications with those performing the trial.

System Description

Figure 4:
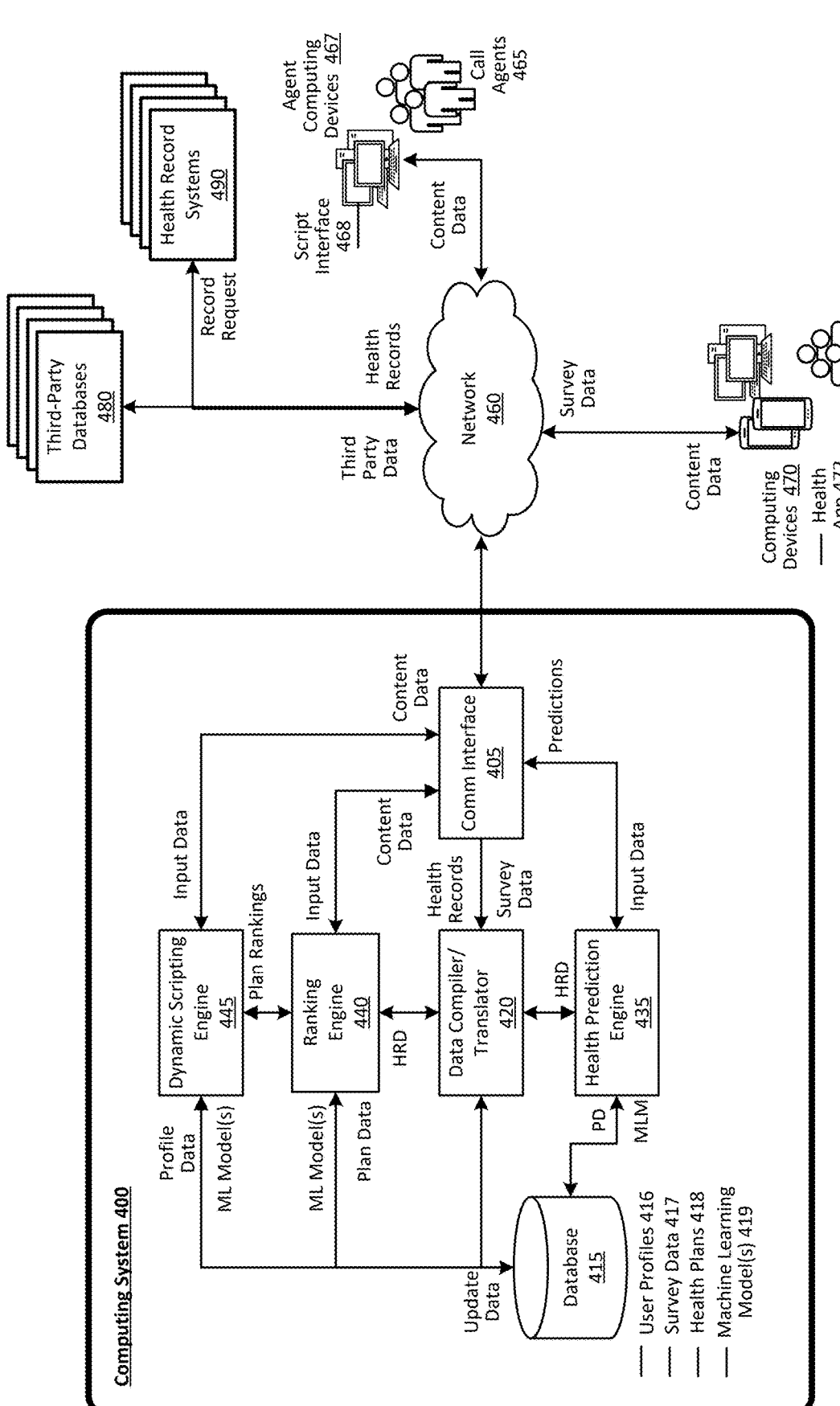
FIG. 4 illustrates a computing system implementing automatic health record compiling, code translation, and dynamic scripting for call agents in connection with a health service, in accordance with examples described herein.

FIG. 4 illustrates a computing system implementing automatic health record compiling, code translation, and dynamic scripting for call agents in connection with a health service, in accordance with examples described herein. The computing system 400 can include a communication interface 405 to communicate, over one or more networks 460, with third-party databases 480, health record systems 490, agent computing devices 467, and computing devices 470 of users 475 of a network-based health service. In various implementations, the computing system 400 can further include a dynamic scripting engine 445 that communicates with the agent computing devices 467 to provide a script interface 468 that call agents 465 may interact with during call sessions with users 475.

In certain examples, the users 475 can access the network-based health service via a health service application 472 or a website on their computing devices 470 to provide personal information, view and select health care coverage plans, link health care accounts (e.g., to enable the computing system 400 to compile health records of the user 475), and provide survey data 417 corresponding to the user's current health care coverage. In certain examples, the users 475 can access the health service to provide survey data 417 including, without limitation, the users' personal experiences, preferences, and/or shortcomings of their current health care plans, such as experience with doctors, health care facilities, costs, health care service, customer service, and the like. The computing system 400 can further include a database 415 for storing user profiles 416 of the users 475, the survey data 417, a full suite of health care coverage plans 418, and one or more machine learning models 419 for optimizing the scoring and ranking of health care coverage plans for each user 475.

When a user 475 provides the appropriate permissions, a data compiler and translator 420 of the computing system 400 can access health record systems 490 of health care providers and insurers of the user 475 to obtain the health records of the user 475. In various examples, the data compiler and translator 420 can automatically translate the codes in which the health records are formatted stored to, for example, provide the user 475 with plain language translations of the user's health records, and perform the health care coverage optimizations described herein. In various examples, the computing system 400 can also include a health prediction engine 435 that can process the health records, and any additional information of the user 475 (e.g., location, demographics, age, weight, etc.) to generate one or more health predictions for the user 475, which can be stored and periodically updated in the user profile 416 of the user 475.

As provided herein, the health records can be obtained by the health record translator 420 when the user 475 links or otherwise synchronizes accounts of the health record systems 490 with the computing system 400. For example, the user 475 can access the health application 472 or website of the health service implemented by the computing system 400 and provide login information, relevant passwords, and/or other authorizations to enable the health record translator 420 to access the user's health records from the health record systems 490. In various implementations described herein, this information can also be provided to a call agent 465 during a call session with the user 475.

In certain implementations, the data compiler and translator 420 can further access third-party databases 480 to compile additional user information, such as census databases, social media services, search engine databases, and the like. Such information can include any publicly available information of the user 475 as well as information obtained based on authorizations provided by the user 475, such as lifestyle information, income and other financial information, and the like. Such information can also be stored in the user's profile 416, and utilized by the computing system 400 in prioritizing leads for the call agents 465 in contacting users 475 who may be interested in obtaining or changing health care coverage.

In some examples, the user profile 416 can include information that is predictive of whether a particular user 475 would be interested in changing health care coverage. For example, the user profile 416 may include information indicating that the user 475 has recently moved or is planning on moving to a new location. The user profile 416 may further indicate whether the user 475 has received a pay increase and/or whether the user 475 has lost government benefits for purchasing health care coverage (e.g., subsidies, expired coverage, moving from government employment to private employment, etc.). In prioritizing leads for call agents 465, the computing system 400 can calculate a confidence score for listed users 475 indicating, based on all gather information, a probability or confidence interval that the user 475 will change a health care coverage plan or obtain a new health care coverage plan. Accordingly, when a call agent 465 accesses the script interface 468, a prioritized list of users 475 can be presented with contextual information concerning each of the users 475, and/or the probability or confidence interval indicating a likelihood that the user 475 will engage with the call agent to purchase an optimal health care coverage plan.

When a call agent 465 initiates contact with a user 475, the call agent 465 can interact with a script interface 468 presented on an agent computing device 467. The dynamic scripting engine 442 of the computing system 400 can dynamically communicate, over the one or more networks 460 with the dynamic scripting engine 445, which can generate a script on the script interface 468 for the call agent in real time based on acquired information. The script interface 468 can initially present the user's personal information, any useful contextual information (e.g., the user 475 has reached retirement age and is eligible for Medicare, the user 475 has moved to a new location, the user 475 has had a recent change in a family situation, and the like). In certain examples, the dynamic scripting engine 445 can execute call monitoring logic to programmatically monitor the interactions between the call agent 465 and the user 475, and adapt the dynamic scripting accordingly. For example, the dynamic scripting engine 445 can monitor the conversation to determine when to provide script language for general conversation, information gathering, transitions, and providing a ranked list of health care plans. In certain implementations, the dynamic scripting engine 445 can further determine an emotional state of the user 475 during the call at any given time, or the call agent 465 can provide inputs indicating the user's emotional state, which can comprise triggers for the dynamic scripting engine 445 in generating the script for the call agent 465.

During the call session, the scripting engine 468 can provide the call agent with the actual words to say to the user 475, and/or can provide suggested questions and responses as an assistance tool for the call agent 465. In one example, as the call session progresses, the call agent 465 can provide inputs on the script interface 468 to, for example, input information provided by the user 475 and indicate when a particular information gathering task has been completed (e.g., when the user 475 has provided authorization to access the user's health records). As input data is provided by the call agent 465 via the script interface 468, the dynamic scripting engine 445 can process the inputs to continue progressing the script for the call agent 465.

Once the user 475 provides the necessary authorizations to access the user's health records, the data compiler and translator 420 can access the relevant health record systems 490 to obtain the user's health records. For example, the data compiler and translator 420 can execute IVR monitoring to detect when the user 475 assents to a vocal request for health record access, or can respond to an input from the call agent 465. As described above, the health records may be stored in coded form, such as CPT codes for indicating the user's prescription information and ICD codes for indicating the user's historical diagnoses. In real time, the data compiler and translator 420 can execute code translation logic to process the coded information in the health records and provide plain language translations of the coded data to the dynamic scripting engine 445, which can automatically populate the script interface 468 with plain language information concerning the user's health records.

In conjunction with the scripting engine 445 updating the script interface 468 for the call agent 465, the health prediction engine 435 and ranking engine 440 can also process the user's health record data (HRD) to generate a set of health predictions for the user 475 and begin scoring the various benefits and/or attributes of available health plans 418 to begin converging on a most optimal health plan 418 for the user 475 respectively. In certain aspects, the dynamic scripting engine 445 can further update the script interface 468 for the call agent 465 to ask the user 475 if the user 475 is experiencing any current difficulties, if the user 475 has any short or long-term health goals, whether the user 475 is able to take time off from work for health care facility visits, whether the user 475 requires mobility or health-related assistance or would prefer assistance, whether the user prefers a particular language for the user's health care providers and documents, and the like. Each of the health prediction engine 435, the ranking engine 440, and the dynamic scripting engine 445 can process the user's responses to these questions and update the health outcome predictions, health plan rankings, and dynamic script accordingly.

In further examples, the dynamic scripting engine 445 can instruct the call agent 465 to verify certain aspects of the user's health record data, such as, without limitation, whether the user 475 is currently using all prescribed drugs, the last few appointments or visits to health care facilities, previous health screenings and diagnoses, the current state of diagnoses, current treatment plans, and the like. Additionally or alternatively, the computing system 400 can communicate with the user's doctors or other health care providers to verify the user's health records.

The dynamic scripting engine 445 can further identify any gaps in health care coverage for the user 475 based on the obtained information, such as a lack of diabetes coverage or a lack of endocrinological care in the user's current health care plan. The script interface 468 can be updated to enable the call agent 465 to discuss these gaps in coverage to the user 475 and determine whether the user 475 wishes to close these gaps. These gaps in coverage may also comprise predicted gaps in coverage based on the health outcome predictions generated by the health prediction engine 435. Thus, the script interface 468 can enable the call agent 465 to discuss potential future health issues with the user 475 and whether the user 475 wishes to address the predicted health issues with a health care plan 418 that provides adequate or superior coverage for the predicted health issues.

In further examples, the dynamic scripting engine 445 can identify the user's current health care plan based on the health record data, and prompt the call agent 465 to discuss any shortcomings in the user's current health care plan. In doing so, the health plan ranking engine 440 can identify health care plans 418 that provide more effective coverage (e.g., higher quality and/or lower out-of-pocket costs), which the dynamic scripting engine 445 can process to update the script interface 468 and enable the call agent 465 to provide the user 475 with specifics regarding the shortcomings of the user's current health care plan and the advantages of other health care plans 418 that may be more optimal for the user's current and predicted health situation.

Based on the user's responses, which may be monitored by the dynamic scripting engine 445 or inputted on the script interface 468 by the call agent 465, the ranking engine 440 can update the health plan rankings to reflect the user's preferences. Each health care coverage plan 418 has a unique set of attributes and benefits, such as costs, disease coverages, partnerships with health care providers, preferred or available health care facilities and hospitals, doctor selections and/or associations, preventative care services, etc. As information is compiled through input data from the call agent and via the data compiler 420, the ranking engine 440 can score each of the benefits and attributes of each health care plan 418 and generate a dynamic ranking of health care plans 418 as additional data is processed. Accordingly, in real time, the call agent 465 can view a current ranking of health care plans 418 on the script interface 468 and can provide the ranking to the user 475 at any time (e.g., via voice, text message link, email, app or website portal, etc.).

As provided herein, the ranking engine 440 can score health plan benefits and attributes based on affordability (e.g., based on the user's current financial information, such as income and expenses), deductibles and copays, familial coverage, the user's current health (e.g., current treatments, diagnoses, prescriptions, etc.), completing a circle of care for the user 475 and/or user's family, predicted health issues for the user 475, and/or the user's own preferences (e.g., as determined via the call session and/or any survey data completed by the user 475). The user 475 can select from a list of highest ranked health plans 418 and/or can opt to choose the highest ranked, most optimal health plan 418, which can trigger a process between the user 475 can call agent 465 to cancel the user's current plan and/or enroll in the selected or most optimal plan 418.

It is contemplated that any of the dynamic scripting engine 445, ranking engine 440, and health prediction engine 435 can execute one or more machine learning models 419 to continuously improve their functions described herein. Such machine learning models 419 may be tailored and adapted to provide increasingly effective and/or efficient communications between the call agent 465 and user 475, as well as improved health predictions and health plan rankings that are personalized depending on the unique attributes of each user 475.

Example Script Interface

FIGS. 5A and 5B show an example script interface 500 presented to a call agent during a call session with a user, according to various examples. The script interface shown in FIGS. 5A and 5B can correspond to the script interface 468 as shown and described with respect to FIG. 4, and can be presented on an agent computing device 467 in real time communication with the computing system 400 of FIG. 4. Furthermore, in the below description of FIGS. 5A and 5B, reference may be made to reference characters representing various features and components described with respect to FIG. 4. Referring to FIG. 5A, the script interface 500 can be presented to the call agent 465 and specify the user 475 that the call agent is contacting. The computing system 400 can obtain any current information of the user 475 and automatically populate certain fields of the script interface 500 for the call agent 465, such as personal information fields (e.g., indicating date of birth, the user's home location, familial information, income details, and any known information about the user's health records.

In various examples, the script interface 400 can include a health record data panel 415 that is to be populated by the user's health record information when obtained. In the example shown in FIG. 4A, the call agent 465 has yet to receive the necessary permissions to access the relevant health record systems 490 to obtain the user's health records. The script interface 500 can include a dynamic script panel 505 that provides the call agent 465 with a script for conversing with the user 475. As provided herein, the computing system 400 dynamically generates the script based on currently acquired information and progresses the call session to obtain additional information of the user 475 that can result in a precise ranking of health plans for the user 475. As the call agent 465 and user 475 converse, the computing system 400 can monitor the call using IVR and auto-populate various fields of the script interface 500 based on the user's responses, and/or the script interface 500 can provide functionality to enable the call agent 465 to input details of the user 475.

In further examples, the script interface 500 can present descriptive connections between particular health conditions and/or prescriptions and specific health plan benefits. As such, the script interface 500 can provide the call agent 465 with tools and/or resources (e.g., search tools or automatic contextual information) that allow the call agent 465 to understand relevant conditions based on the user's health records. In still further examples, the dynamic script 505 can automatically present follow-up questions for the call agent 465 that enables the call agent 465 to acquire more information from the user 475, such as the severity of a particular health condition.

The script interface 500 can further include a health plan ranking panel 510 that provides a health plan ranking (e.g., in real time) for the call agent 465 based on all currently acquired information of the user 475. In the example shown in FIG. 5A, the call agent 465 is tasked with presenting a conversational tone with the user 475 while advancing the call session in a strategic manner, such that the necessary information from the user 475 is received naturally and in a sincere manner.

Referring to FIG. 5B, the script interface 500 has been updated based on the progression of the call session, with each of the dynamic script panel 505, the health record data panel 515, and the health plan ranking panel 510 having been updated based on newly obtained information pertaining to the user 475. As shown in the dynamic script panel, 505, the call agent 465 and user 475 have discussed authorization to obtain the user's health records, which has been granted by the user 475. Upon receiving the authorization, the backend computing system 400 automatically accesses the health record systems 490 and obtains the user's health records. The computing system 400 also automatically translates the coded health records and populates the health record data panel 515 accordingly.

Furthermore, based on the health record data being obtained, the computing system 400 can automatically update the health plan rankings 510 for the user 475. As provided herein, the dynamic script 505 can continue with the goal of obtaining any additional relevant information (e.g., identifying any gaps in the user's current coverage, determining the user's health goals, moving situation, whether the user 475 would be interested in relocating closer to family, and the like). As shown in the script interface 500, and based on the user's current information, the computing system 400 has determined that the most optimal plan for the user 475 is a specific special needs plan that is highly tailored to the user's unique medical and health situation. At a later stage of the call session, the call agent 465 and user 475 can discuss the top plans 418 for the user 475 and initiate a process to cancel the user's current plan and/or purchase a plan 418 that is selected by the user 475.

Methodology

Figure 6:
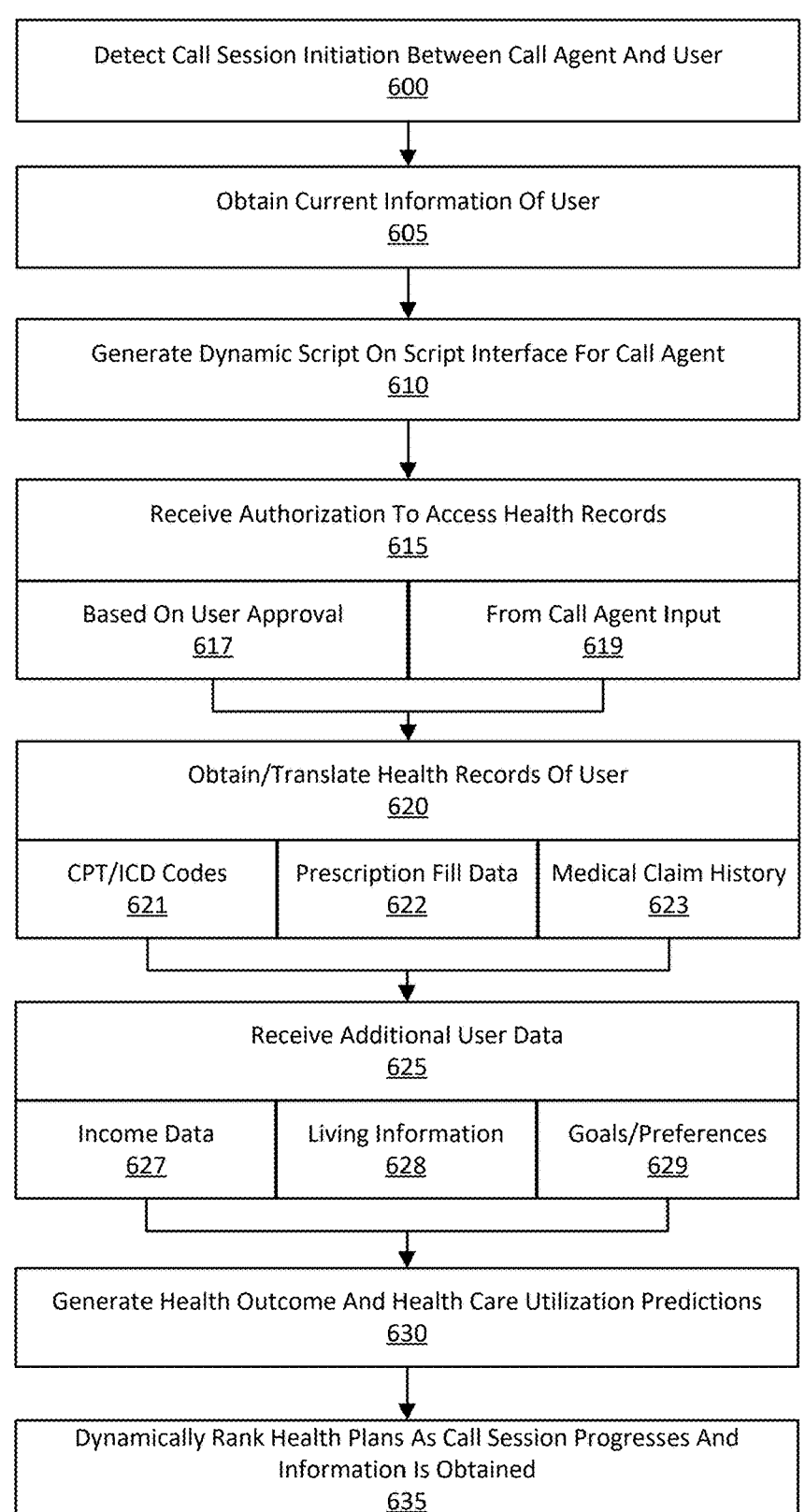
FIG. 6 is a flow chart describing a method of dynamic scripting during a call session between a call agent and a user, according to various examples.

FIG. 6 is a flow chart describing a method of dynamic scripting during a call session between a call agent 465 and a user 475, according to various examples. In the below discussion of FIG. 6, reference may also be made to reference characters representing certain features and components as shown and described with respect to FIGS. 4, 5A, and 5B. Furthermore, the processes described with respect to FIG. 6 may be performed by a backend computing system 400, agent computing device 467, or a combination of both. Still further, while the steps in FIG. 6 are shown in a specific order, each step described may be performed prior to, in conjunction with, or subsequent to any other step. Referring to FIG. 6, the computing system 400 can detect a call session being initiated between a call agent 465 and a user 475 (600). In response to detecting the call session being initiated, the computing system 400 can obtain any current information pertaining to the user (e.g., as accessed through third-party databases 480, such as driving records, census data, social media data, demographic information, income data, etc.) (605), and generate a dynamic script 505 on a script interface 500 presented on the agent's computing device 467 (610).

As the call agent 465 and user 475 converse, the computing system 400 can receive authorization to access the user's health records (615). For example, the computing system 400 can automatically detect the user 475 providing approval and/or authorization during the call session (617), or can receive authorization based on call agent input (619). In further examples, the user 475 can link various health accounts with the computing system 400 that enables the computing system 400 to access the user's health records.

The computing system 400 then obtains and translates or decodes the user's health records from the relevant health record systems 490 (620). As described above, the health records may be in coded form, such as CPT and ICD codes for the user's prescription and diagnoses information (621). Thus, the computing system 400 automatically translates the codes into plain language and auto-populates the call agent's script interface 500 accordingly. As further described above, the health records of the user 475 can describe the user's prescription information as well as provide a full corpus of the user's medical history. The prescription information can include the user's prescription fill history (622), which comprises all prescribed medications, prescription schedules, prescription lapses or cancelations, and/or dates and times when prescriptions are filled (e.g., indicating whether the user 475 is taking medications as prescribed). The user's medical history can include the user's medical claim history, which can comprise all payment requests submitted to the user's insurance provider(s), any copays for health care facility visits or pharmacy orders, and/or insurance claims made by the user 475.

As the call session continues to progress, the call agent 465 can be provided with a script to determine any additional relevant user data (625), such as income information (627), current and/or future living information (628), and/or the user's health-related goals and any preferences, such as preferred doctors, health care facilities, pharmacies, etc. (629). In certain examples, the computing system 400 can further generate health outcome and health care utilization predictions for the user 475 based on the user's current information and medical history (630). For example, a health record indicating that the user 475 is overweight or obese may be predictive of a future diagnosis for diabetes and/or predictive that the user 475 will require one or more prescriptive medications at some point in the future. In further examples, the health care utilization predictions can provide likelihoods or probabilities that the user 475 will require additional medical items including, without limitation, health care facility visits, screenings, treatment plans, prescriptions, and the like. As information is obtained, the computing system dynamically ranks health plans 418 for the user 475 (635).

The result is the most optimal plan for the user 475 being ranked at the top of the health plan ranking panel 510 of the script interface 500. The call agent 465 can provide the list to the user 475, either verbally or via electronic communication (e.g., text link, email, etc.). Thereafter, the user 475 can view the details of each plan (e.g., coverages, copays, deductibles, health care facilities, doctors, prescriptions, etc.) and choose a plan that is most suitable to the user's needs and concerns. It is contemplated that when individuals are paired with health care plans that are optimized to their unique needs and health situations, health care costs to the user 475 as well as costs to society may be dramatically reduced while increasing the quality of care.

System Description

Figure 7:
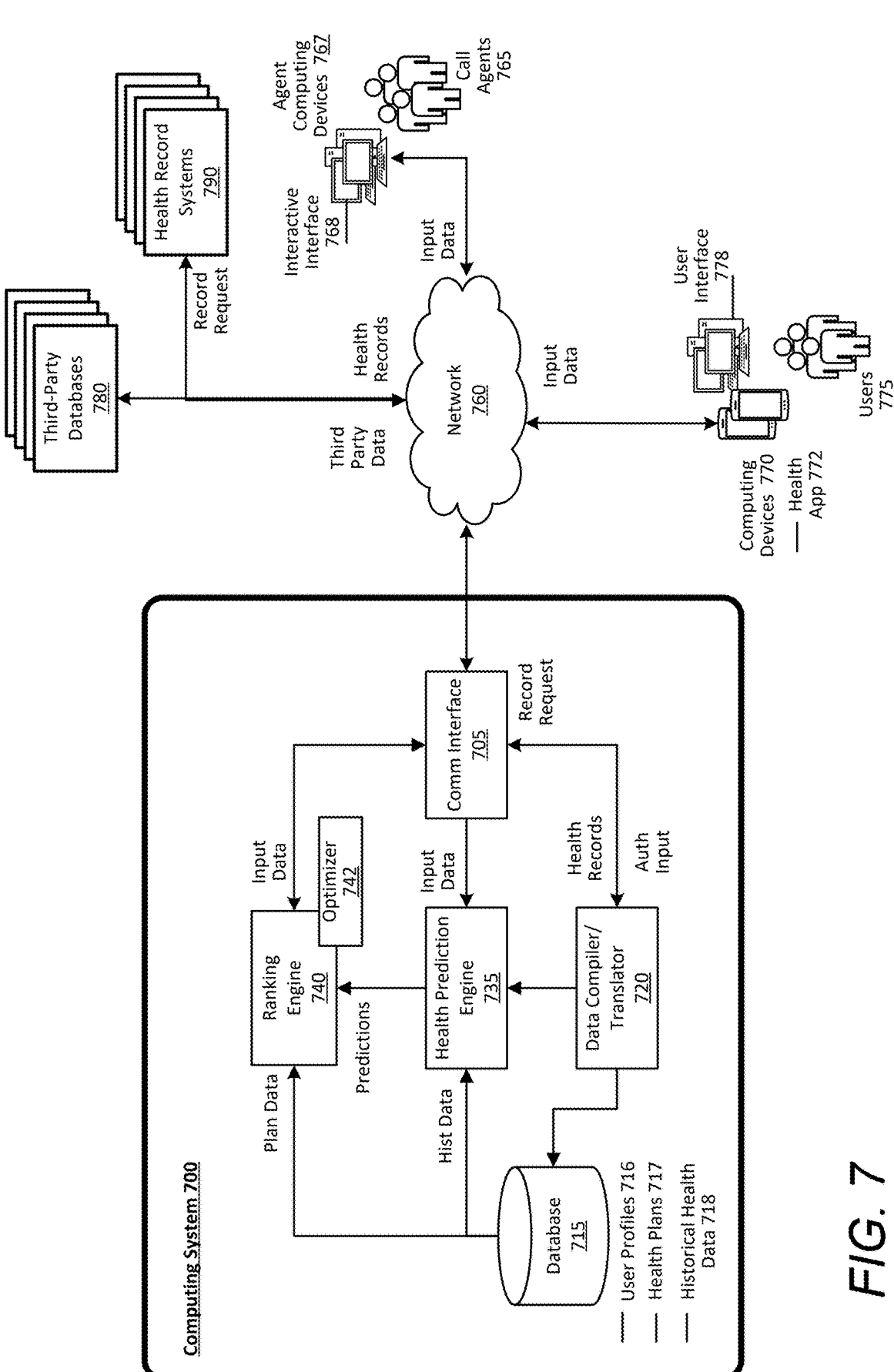
FIG. 7 illustrates a computing system implementing automatic health record compiling, code translation, health prediction, and health plan ranking for users, in accordance with examples described herein.

FIG. 7 illustrates a computing system 700 implementing automatic health record compiling, code translation, health prediction, and health plan ranking for users, in accordance with examples described herein. The computing system 700 can include a communication interface 705 to communicate, over one or more networks 760, with third-party databases 780, health record systems 790, agent computing devices 767, and/or computing devices 770 of users 775 of a network-based health service. As provided herein, the call agents 765 can operate agent computing devices 767 to present an interactive agent interface 768 that provides the call agents 765 with supportive information for each call session, such as dynamic scripting and interactive features that enable the call agent 765 to provide inputs based information received from the user 775 and/or the user's health records.

In certain examples, the users 775 can access the network-based health service via a health service application 772 or a website on their computing devices 770 to provide personal information, view and select health care coverage plans, link health care accounts (e.g., to enable the computing system 700 to compile health records of the user 775), provide survey data corresponding to the user's current health care coverage, and the like. In certain examples, the users 775 can access the health service to provide survey data including, without limitation, the users' personal experiences, preferences, and/or shortcomings of their current health care plans, such as experience with doctors, health care facilities, costs, health care service, customer service, and the like. The computing system 700 can further include a database 715 for storing user profiles 716 of the users 775, survey data, a full suite of health care coverage plans 717, and historical health data 718 that can indicate health correlations that enable a health prediction engine 735 of the computing system 700 to predict a particular user's health care needs over a future time frame (e.g., with the next year).

When a user 775 provides the appropriate permissions (e.g., a HIPAA authorization provided verbally and selected by the call agent 765 on the interactive agent interface 768, and/or a blue button selection by the user 775), a data compiler and translator 720 of the computing system 700 can access health record systems 790 of health care providers and insurers of the user 775 to send record requests and obtain the health records of the user 775. In various examples, the data compiler and translator 720 can automatically translate the codes in which the health records are formatted stored to, for example, provide the user 775 and/or call agent 765 with plain language translations of the user's health records, and perform the health care coverage optimizations described herein. In various examples, the computing system 700 can also include a health prediction engine 735 that can process the health records, historical health data 718, and any additional information of the user 775 (e.g., location, demographics, age, weight, etc.) to generate one or more health predictions for the user 775, which can be stored and periodically updated in the user profile 716 of the user 775.

As provided herein, the health records can be obtained by the health record translator 720 when the user 775 links or otherwise synchronizes accounts of the health record systems 790 with the computing system 700. For example, the user 775 can access the health application 772 or website of the health service implemented by the computing system 700 and provide login information, relevant passwords, and/or other authorizations to enable the health record translator 720 to access the user's health records from the health record systems 790. In various implementations described herein, this information can also be provided to a call agent 765 during a call session with the user 775.

In certain implementations, the data compiler and translator 720 can further access third-party databases 780 to compile additional user information, such as census databases, social media services, search engine databases, and the like. Such information can include any publicly available information of the user 775 as well as information obtained based on authorizations provided by the user 775, such as lifestyle information, income and other financial information, and the like. Such information can also be stored in the user's profile 716, and can be utilized by the computing system 700 in prioritizing leads for the call agents 765 in contacting users 775 who may be interested in obtaining or changing health care coverage.

When a call agent 765 initiates contact with a user 775, the call agent 765 can interact with an interactive agent interface 768 presented on an agent computing device 767. In some aspects, the interactive agent interface 768 can include a dynamic script that the call agent 765 may reference in communicating with the user 775. Additionally or alternatively, the interactive agent interface 768 can present the call agent 765 with a set of interactive features that the call agent 765 can update based on the progression of the call session with the user 775.

In various examples, once the user 775 provides the necessary authorizations to access the user's health records, the data compiler and translator 720 can access the relevant health record systems 790 to obtain the user's health records. In some examples, the data compiler and translator 720 can execute IVR monitoring to detect when the user 775 assents to a vocal request for health record access, or can respond to an input from the call agent 765. In further examples, the authorization can be provided via a texted link that, when selected by the user 775, provides the data compiler and translator 720 with the necessary authorization to access the user's health records. As described above, the health records may be stored in coded form, such as CPT codes for indicating the user's prescription information and ICD codes for indicating the user's historical diagnoses. In real time, the data compiler and translator 720 can execute code translation logic to process the coded information in the health records and present plain language translations of the coded data to the call agent 765 via the interactive agent interface 768.

In certain examples, the call agent 765 can further verify certain aspects of the user's health record data, such as, without limitation, whether the user 775 is currently using all prescribed drugs, the last few appointments or visits to health care facilities, previous health screenings and diagnoses, the current state of diagnoses, current treatment plans, and the like. Additionally or alternatively, the computing system 700 can communicate with the user's doctors or other health care providers to verify the user's health records.

In various implementations, the health prediction engine 735 can process the user's health record data and historical health data 718 to generate a set of health predictions for the user 775. Specifically, the health prediction engine 735 can execute a machine learning model and/or implement artificial intelligence techniques that process health record data of a particular user 775 and historical health data 718 of any number of patients to generate a set of health predictions for the user 775. For example, the health prediction engine 735 can identify any correlations between the user 775 and any number of other patients' historical health information (e.g., age, demographics, genetic background, gender, similar lab results, diagnoses, and prescriptive medications, etc.) to generate the set of health predictions for the user 775. The health predictions can further include predicted health care requirements and coverage needs for the user 775 over a future time period. In further implementations, the health prediction engine 735 can utilize the health outcome predictions to further predict a set of future health care needs of the user 775, future medications, medical devices (e.g., a wheelchair or CPAP), etc. The health prediction engine 735 can further estimate a set of costs for the user 775 based on this information, and can provide the estimated costs and predictions to the ranking engine 740, which can provide the user 775 and/or call agent 765 with a recommended health care plan accordingly. In still further implementations, the ranking engine 740 can utilize aggregated anonymous data to determine known health outcomes of patients for a health care network or group of doctors to further generate the health plan rankings. In further examples, CMS data and star rankings can further be utilized to generate the health plan rankings.

As provided below with respect to FIGS. 8A through 8D, the interactive agent interface 768 can be updated with information provided by the computing system 700 (e.g., based on the user's health records), and can guide the call agent 765 to request additional information, such as which doctors the user 775 wishes to keep (e.g., primary care doctor and specialists), which medications and pharmacies the user 775 wishes to keep, and any current or potentially future diagnoses of the user 775. As the call agent 765 and user 775 discuss such information, the call agent 765 can input the information into the interactive agent interface 768, which can affect the predictions generated by the health prediction engine 735 and/or the health plan rankings generated by the ranking engine 740. Accordingly, the inputs provided by the call agent 765 are received by each of the health prediction engine 735 and the optimizer 742 of the ranking engine 740 as input data, which are processed by each to update the health predictions and health plan rankings accordingly.

As provided herein, the user's health records can indicate a set of past and current diagnoses, lab results, treatments, and/or prescriptions of the user 775. In certain implementations, the health prediction engine 735 can identify historical health records in the historical health data 718 that include the same or similar diagnoses, lab results, treatments, and/or prescriptions, and determine whether this information leads to further diagnoses, treatments, and/or prescriptions. The health prediction engine 735 can further filter the historical records based on the user's personal information, such as age, gender, genetic information, and the like, and can determine the actual health outcomes of the individuals associated with closely matching historical health records. The health prediction engine 735 may then determine a set of probable health outcomes for the user 775, which can include future treatments, diagnoses, likely medications, health coverage needs, and the like. In some aspects, the health prediction engine 735 can associate each predicted health outcome (e.g., future diagnosis, treatments, prescription, etc.) with a probability or probabilistic score, which can be utilized by a ranking engine 740 to score or apply weightings to the various benefits and attributes of the health plans 717 for the user 775.

In various implementations, the ranking engine 740 of the computing system 700 can execute an optimizer 742 (e.g., a machine learning or artificial intelligence application) using the health predictions of the user 775 from the health prediction engine 735 and the health records of the user 775 to score the various benefits and/or attributes of available health plans 717 for the user 775. In certain aspects, the call agent 765 can reference a dynamic script presented on the interactive interface 768 to ask the user 775 if the user 775 is experiencing any current difficulties, if the user 775 has any short or long-term health goals, whether the user 775 is able to take time off from work for health care facility visits, whether the user 775 requires mobility or health-related assistance or would prefer assistance, whether the user prefers a particular language for the user's health care providers and documents, and the like. Each of the health prediction engine 735 and the ranking engine 740 can process the user's responses to these questions, as inputted by the call agent 765 in the interactive interface 768 and update the health outcome predictions and health plan rankings accordingly.

In various implementations, the optimizer 742 can further identify any current or future gaps in health care coverage for the user 775 based on the obtained information from the user 775 and health predictions, such as a lack of diabetes coverage or a lack of endocrinological care in the user's current health care plan. The interactive agent interface 768 can guide the call agent 765 to discuss these gaps in coverage to the user 775 and determine whether the user 775 wishes to close these gaps. These gaps in coverage may also comprise predicted gaps in coverage based on the health outcome predictions generated by the health prediction engine 735. Thus, the call agent 765 can discuss potential future health outcomes and/or future health plan coverage needs with the user 775 based on the health predictions and determine whether the user 775 wishes to address the predicted health issues with a health care plan 717 that provides adequate or superior coverage for the predicted health outcomes. As stated herein, the predict health outcomes can comprise predicted future diagnoses, necessary treatments and/or prescriptions, and the like.

In further examples, the interactive agent interface 768 can present the user's current health care plan based on the health record data and prompt the call agent 765 to discuss any shortcomings in the user's current health care plan. The health plan ranking engine 740 can further identify and rank health care plans 717 that provide more effective coverage (e.g., higher quality and/or lower out-of-pocket costs). In certain implementations, the ranking engine 740 can update the health plan rankings to reflect the user's preferences. Each health care coverage plan 717 has a unique set of attributes and benefits, such as costs, disease coverages, partnerships with health care providers, preferred or available health care facilities and hospitals, doctor selections and/or associations, preventative care services, etc. As information is compiled through input data from the call agent 765 and via the data compiler 720, the ranking engine 740 can score each of the benefits and attributes of each health care plan 717 and generate a ranking of health care plans 717 in comparison to the user's current health care plan. Accordingly, the call agent 765 can view a current ranking of health care plans 717 on the interactive interface 768 and can provide the ranking to the user 775 at any time (e.g., via voice, text message link, email, app or website portal, etc.).

As provided herein, the ranking engine 740 can score health plan benefits and attributes based on affordability (e.g., based on the user's current financial information, such as income and expenses), deductibles and copays, familial coverage, the user's current health (e.g., current treatments, diagnoses, prescriptions, etc.), completing a circle of care for the user 775 and/or user's family, predicted health outcomes for the user 775, and/or the user's own preferences (e.g., as determined via the call session and/or any survey data completed by the user 775). The user 775 can select from a list of highest ranked health plans 717 and/or can opt to choose and enroll in any of the listed plans, such as the highest ranked, most optimal health plan 717, which can trigger a process between the user 775 can call agent 765 to cancel the user's current plan and/or enroll in the selected or most optimal plan 717.

It is contemplated that the health prediction engine 735 and ranking engine 740 can execute one or more machine learning models or artificial intelligence applications to continuously improve their functions described herein. Such machine learning models and artificial intelligence applications may be tailored and adapted to provide increasingly effective and/or efficient communications between the call agent 765 and user 775, as well as improved health predictions and health plan rankings that are personalized depending on the unique attributes of each user 775.

Additionally or alternatively, a user 775 can access a website or launch an application that provides an interactive user interface 778 that enables the user 775 to provide an authorization input that triggers the data compiler and translator 720 to obtain and translate the user's health records from the health record systems 790 in the manner described above. The interactive user interface 778 further provides navigable screens (e.g., similar to the interactive agent interface 768) that prompts the user 775 to verify health records, confirm or select pharmacy information and preferences, select preferred pharmacies, confirm and/or select prescription medications, confirm doctor and/or clinic information and preferences, select preferred doctors and/or clinics, confirm past and/or current diagnoses, provide additional diagnosis information, and the like.

In conjunction with or upon receiving the input data indicating the user's selections from the user's computing device 770, the health prediction engine 735 can generate a set of health predictions and the ranking engine 740 can further perform the health plan benefit and attribute optimizations and rankings for the user 775 in the manner(s) described throughout the present disclosure. The user 775 can view comparisons between the ranked health care plans and the user's current health care plan, including benefit and cost comparisons, and select to enroll in one of the ranked health care plans. Further description of the interactive user interface 778 is provided below with respect to FIGS. 8E through 8H.

Example Interactive Agent Interfaces

Figure 8A:
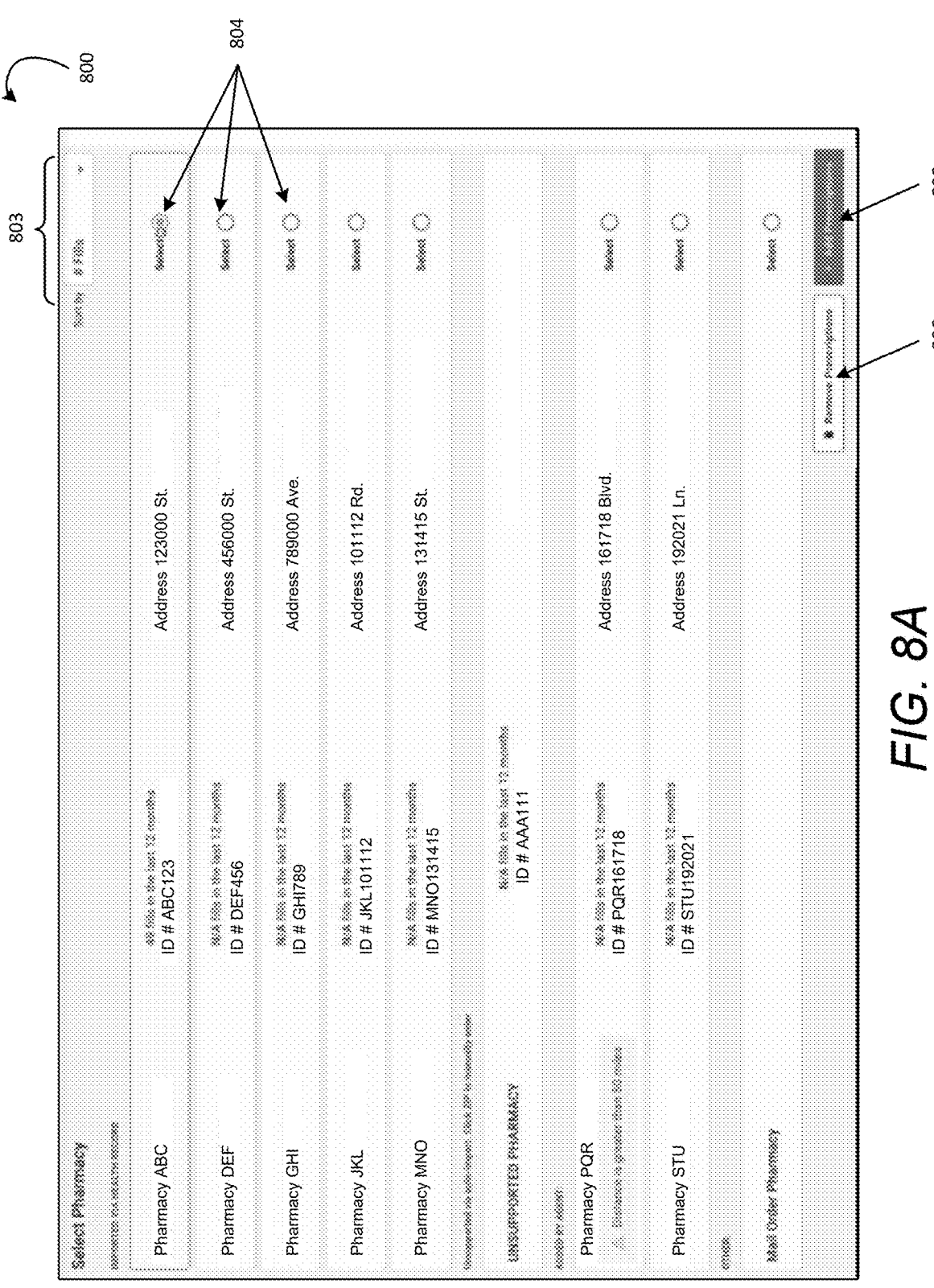
FIGS. 8A through 8D depict example interactive agent interfaces presented to a call agent during a call session with a user, according to various examples.

FIGS. 8A through 8D depict an example interactive agent interface 800 presented to a call agent during a call session with a user, according to various examples. The interactive agent interface 800 can correspond to the agent interface 768 shown and described with respect to FIG. 7. The interactive agent interface 800 can be presented to the call agent in conjunction with a call session between the call agent and the user. The interactive agent interface 800 shown in FIG. 8A may be presented subsequent to an authorization by the user to obtain the user's health records, which can trigger the health prediction and health plan ranking techniques described throughout the present disclosure. Referring to FIG. 8A, the interactive agent interface 800 can provide pharmacy information of the user as imported from the user's health records. During the interaction between the call agent and the user, the call agent can query the user for current pharmacies at which the user acquires prescription medications, as indicated in the prepopulated fields 802. Based on the user's confirmations or answers, the call agent can provide selection inputs on selectable features 804 included on the interactive interface 800.

In the example shown in FIG. 8A, the interactive interface 800 enables the call agent to sort and rearrange the pharmacies imported from the user's health records using a filter menu 803. The prepopulated fields 802 can include information associated with each listed pharmacy (e.g., to jog the user's memory), such as the pharmacy's name and identification number, address, and a number of prescriptions filled at the pharmacy over a given time frame. In some examples, the prepopulated fields 802 can further indicate anomalies, such as when a listed pharmacy is a long distance from the user's home location or when a pharmacy no longer exists or is not supported by any health care plans.

In further examples, the interactive interface 800 includes a selectable feature 806 that enables the call agent to remove a particular prescription, such as when the user no longer requires the prescription. The interactive interface 800 can further include a selectable feature 808 that enables the call agent to include additional prescriptions not listed in the prepopulated fields. As provided herein, the selections provided by the call agent can be processed by the health prediction and ranking engines described with respect to FIG. 7.

Figure 8B:

Referring to FIG. 8B, the interactive agent interface 800 can prompt and guide the call agent to request health-related information from the user. In one step, the interactive agent interface 800 presents a panel 812 that enables the call agent to select whether the user has agreed to provide information regarding prescription medication coverage (e.g., the user's current prescriptions). The interactive interface 800 can further include a text box 814 or selectable menu that enables the call agent to input any preferred pharmacies of the user.

In various examples, the interactive agent interface 800 further includes selectable features 816 that guide the call agent to query whether the user is willing to use a different pharmacy and/or receive medications by mail (e.g., to save the user money). Once medications are confirmed and pharmacy details are inputted by the call agent, an indicator 818 is provided to the call agent indicating that prescription and pharmacy information from the user has been completed. A doctor selection panel 810 is presented to the call agent to confirm the user's preferences for doctors. As shown in FIG. 8B, the doctor selection panel 820 is prepopulated to include the user's current doctors and/or clinics as indicated by the user's health records, and can include details regarding the doctor's or clinic's specialty, a number of visits to each doctor or clinic over a given time frame, an address of the doctor's facilities, and selectable features 822 that enable the call agent to include a particular doctor or clinic, or provide an input indicating that the doctor or clinic is required for the subsequent health plan rankings. As discussed herein, the inputs provided by the call agent can be processed by the health prediction and ranking engines described in connection with FIG. 7.

Figure 8C:
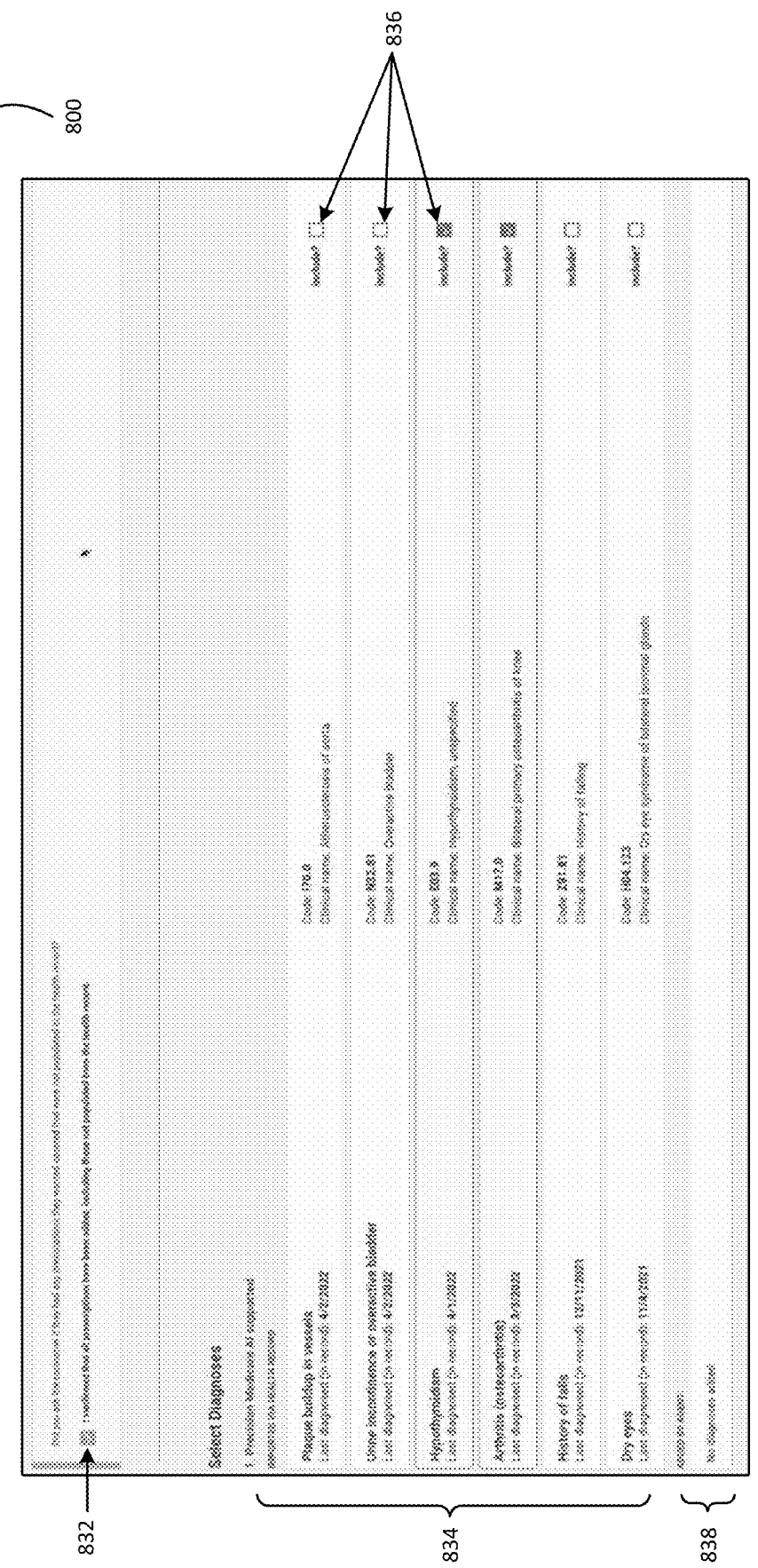

Referring to FIG. 8C, the interactive interface 800 can include a panel that guides the call agent in confirming the user's doctors and prescriptions, and can further include a confirmation feature 832 that enables the call agent to confirm completion of the user's prescriptions. In various examples, the interactive interface 800 may present a set of prepopulated fields 834, based on the user's health records, that indicate the user's past and/or current diagnoses. The call agent is prompted to confirm the user's diagnoses information and provide selections on selectable features 836 included on the interactive interface 800 whether the user confirms a current diagnosis. In certain examples, the interactive interface 800 can also include a text feature 838 that enables the call agent to input any additional diagnoses that have not been prepopulated on the interface 800 (e.g., diagnosis information that has not been included in the user's health records).

Figure 8D:
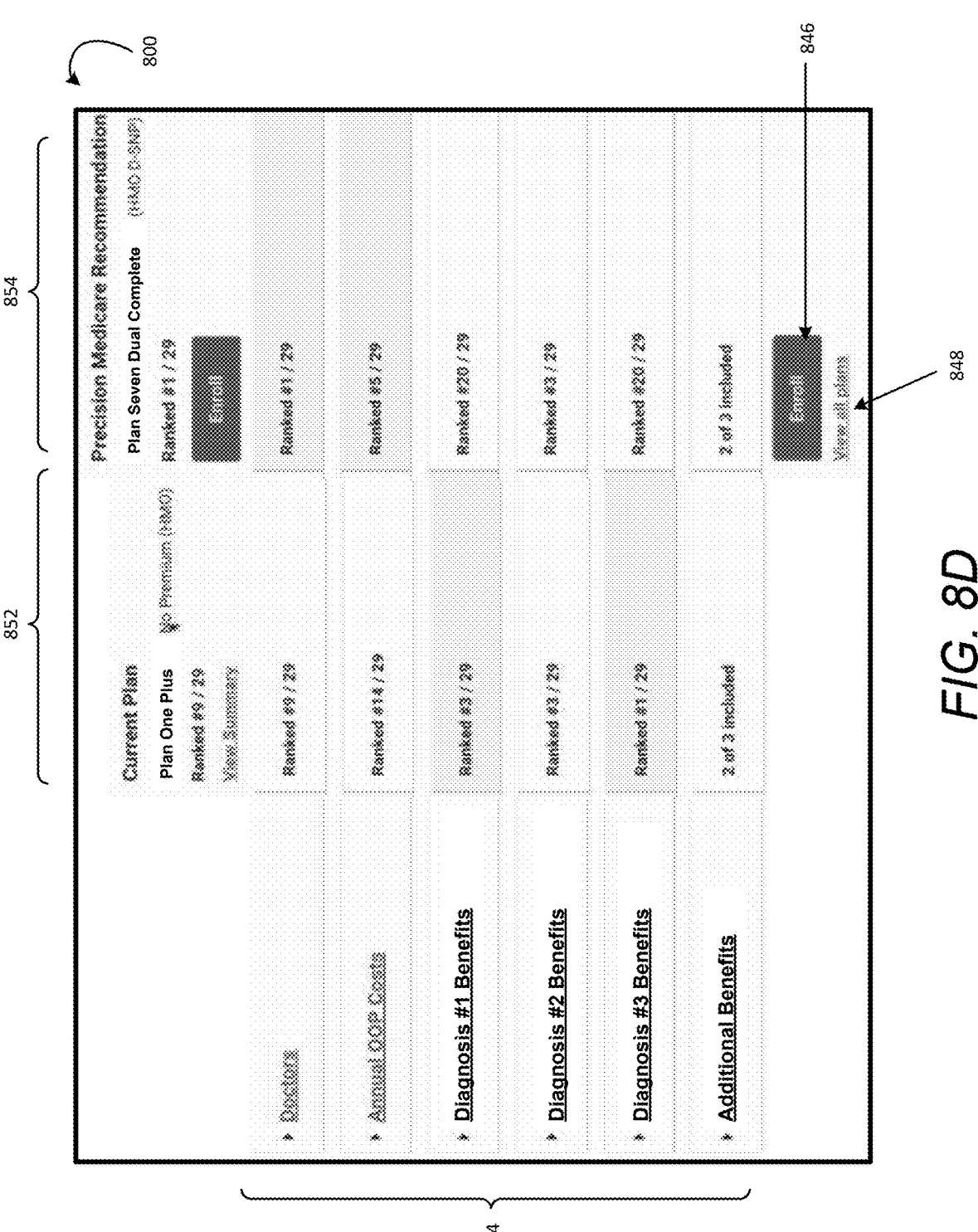

Referring to FIG. 8D, the interactive agent interface 800 can present a most optimal health care plan 854 as determined by the health plan ranking engine based on the health records of the user and the inputs provided by the call agent during the call session. In certain examples, the optimal health care plan 854 can be presented in comparison to the user's current health care plan 852, with a panel 844 indicating further comparisons provided for each prioritized benefit of the user. As described above, the rankings for each of the benefits and attributes of each health care plan can be based on the user's health records, preferences, and the information provided by the user during the call session as inputted by the call agent into the interactive interface 800. As shown in FIG. 8D, the optimal health care plan 854 is parsed into the highest priority benefits and/or preferences of the user (e.g., includes all of the user's preferred doctors at minimal cost).

The rankings and comparisons shown in FIG. 8D can be provided to the user for review (e.g., via an email or text message link), and the user can opt to enroll in the optimal plan by selecting an enroll feature 846. Alternatively, the call agent may receive a verbal or written confirmation that the user wishes to enroll in the optimal plan, and can perform the enrollment via the interactive interface 800. In further examples, the interactive interface 800 can include a selectable feature 848 that enables the call agent or user to view all plans that have been ranking by the ranking engine. Selection of this feature 848 can enable the call agent and/or user to view each of the ranked plans in comparison to the user's current plan, which the attributes and benefits parsed and ranked substantially as shown.

Example Interactive User Interfaces

Figure 8E:
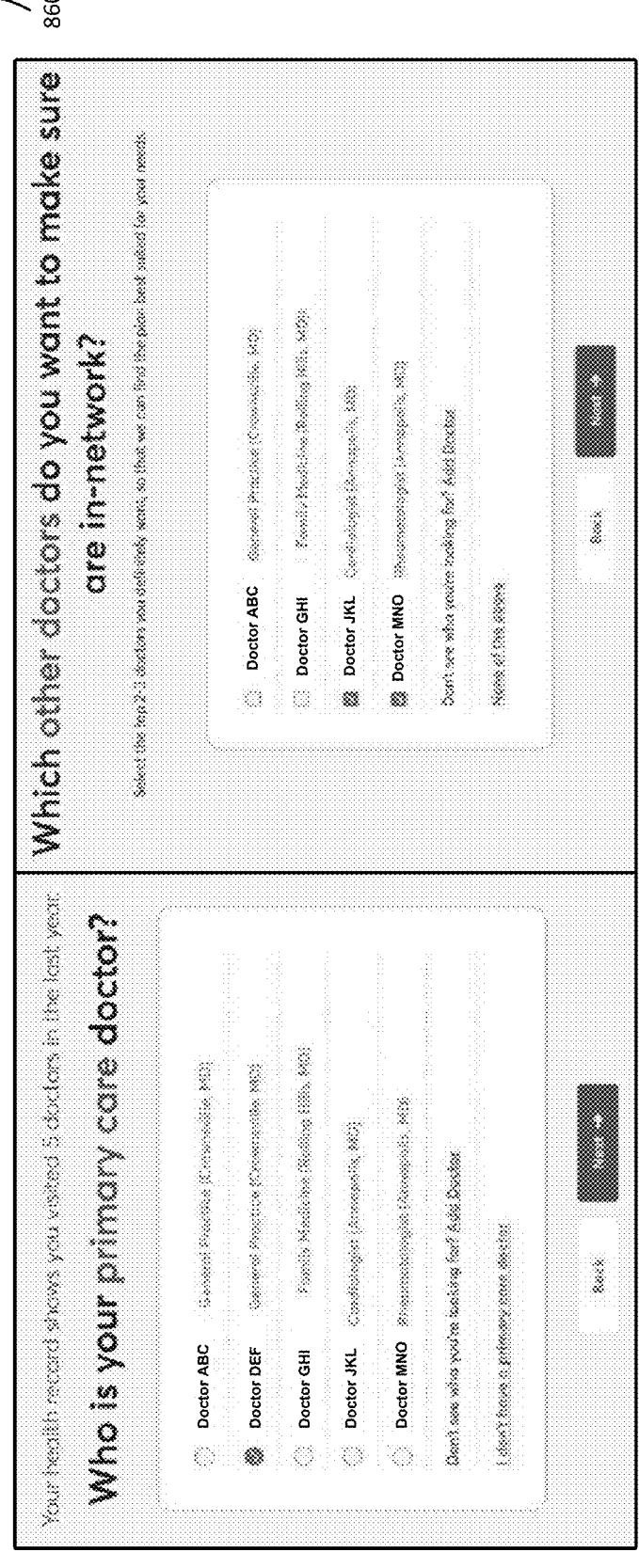

FIGS. 8E through 8H depict example interactive user interfaces presented to users to implement one or more processes described herein. The interactive user interface 860 can correspond to the user interface 778 shown and described with respect to FIG. 7. The interactive user interface 860 can be presented to a user of a network-based health service via an application or web portal provided on the user's computing device 770, as further shown in FIG. 7. The user interface 860 shown in FIG. 8E may be presented subsequent to an authorization by the user to obtain the user's health records, which can trigger the health prediction and health plan ranking techniques described throughout the present disclosure. Referring to FIG. 8E, the user interface 860 can query the user for information pertaining to the user's current and preferred doctors. The interactive user interface 860 can be prepopulated with the user's doctors as identified from the user's health records, and the user can provide selection inputs accordingly.

Figure 8F:
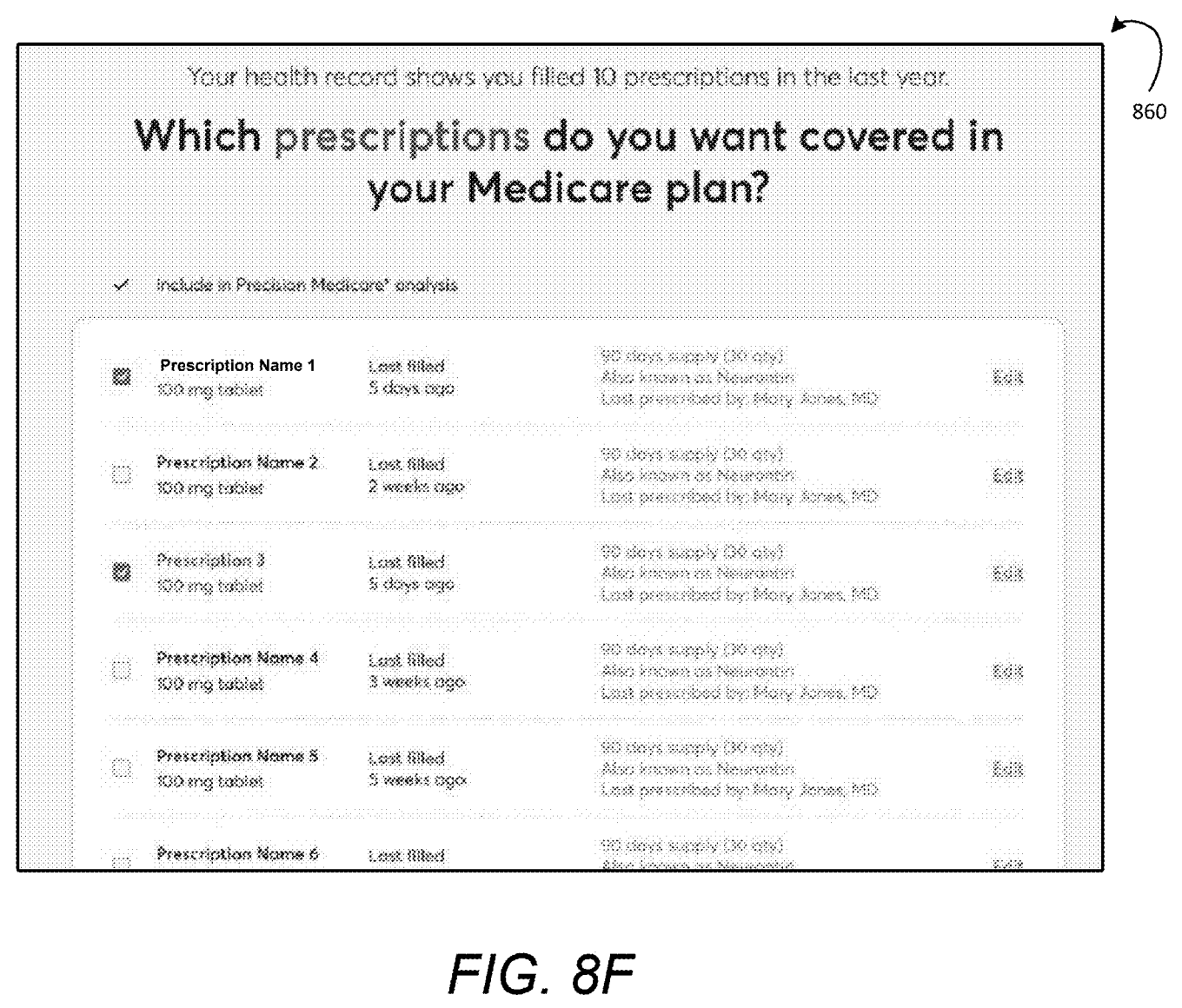
Figure 8G:
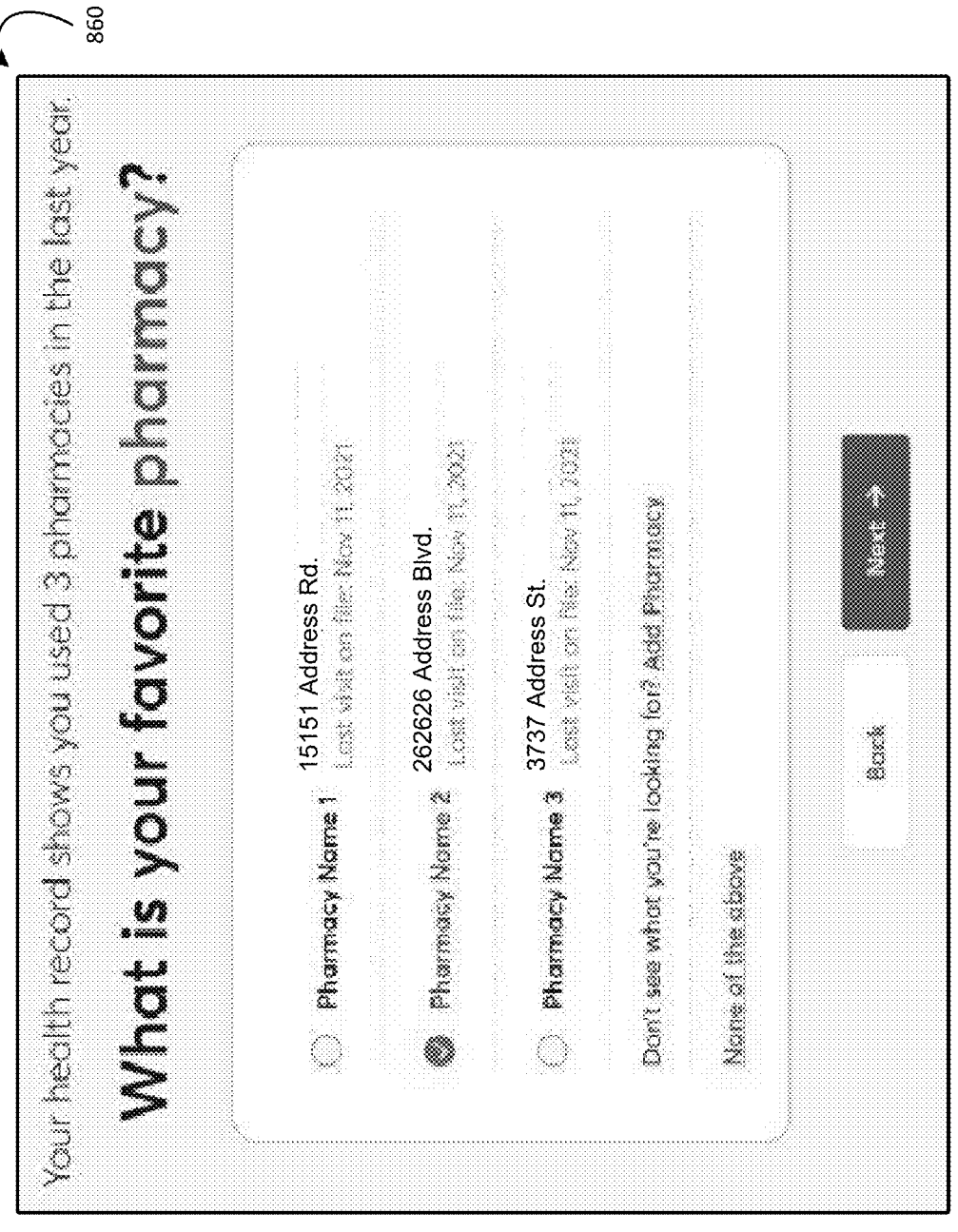
Figure 8H:
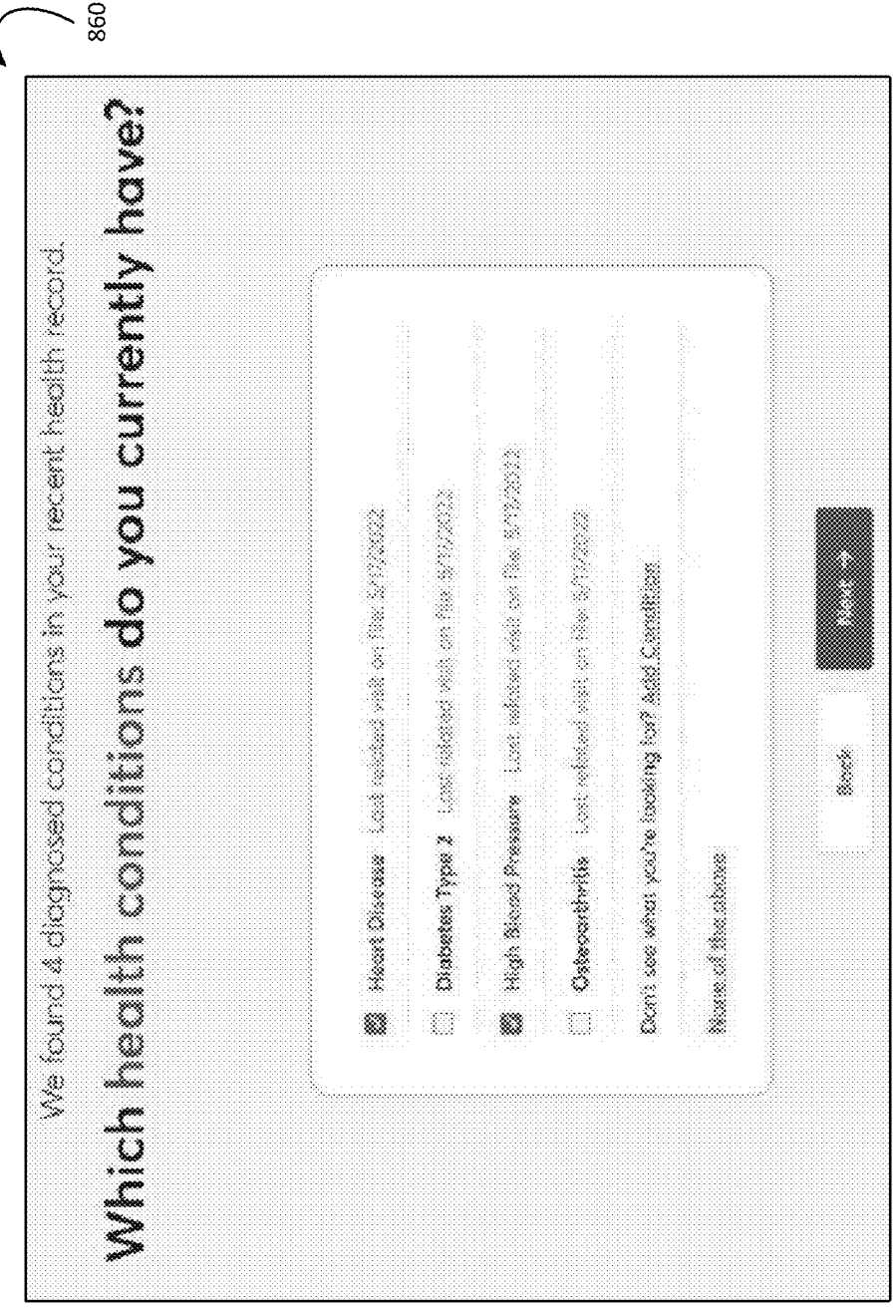

Referring to FIG. 8F, the interactive user interface 860 can query the user for information pertaining to the user's current and/or preferred medications. The medication list shown in FIG. 8F can likewise be prepopulated based on the user's health records, and can further enable the user to provide selection inputs accordingly. FIG. 8G depicts the interactive user interface 860 querying the user for a preferred pharmacy from pharmacies previously visited by the user. The user can provide one or more selection inputs accordingly and proceed to a next screen or scroll to a next portion of the interactive user interface 860. Referring to FIG. 8H, the user is requested to provide information or confirmations pertaining to current diagnoses. As shown in FIG. 8H, the user can select from a prepopulated list based on the health records obtained by the computing system 700 and can add additional diagnoses that have not been included.

The various inputs and selection provided by the user in the interactive user interface 860 shown with respect to FIGS. 8E through 8H can be received by the computing system 700 of FIG. 7 as input data, which is processed by the health prediction engine 735 and ranking engine 740 according to the techniques described herein. Upon performing the health prediction and health plan ranking techniques, the computing system 700 can provide the user with a ranking and comparison screen substantially similar to the interface shown in FIG. 8D. In particular, the ranking and comparison screen can present a ranking of each attribute and/or benefit of a ranked plan (e.g., a most optimal plan versus the user's current plan), can enable the user to view details pertaining to each ranked benefit and/or attribute (e.g., included doctors, medications, pharmacies, etc.), allow the user to view other ranked plans in comparison to the user's current plan, and can enable the user to enroll in a particular health care plan.

Methodology

Figure 9A:
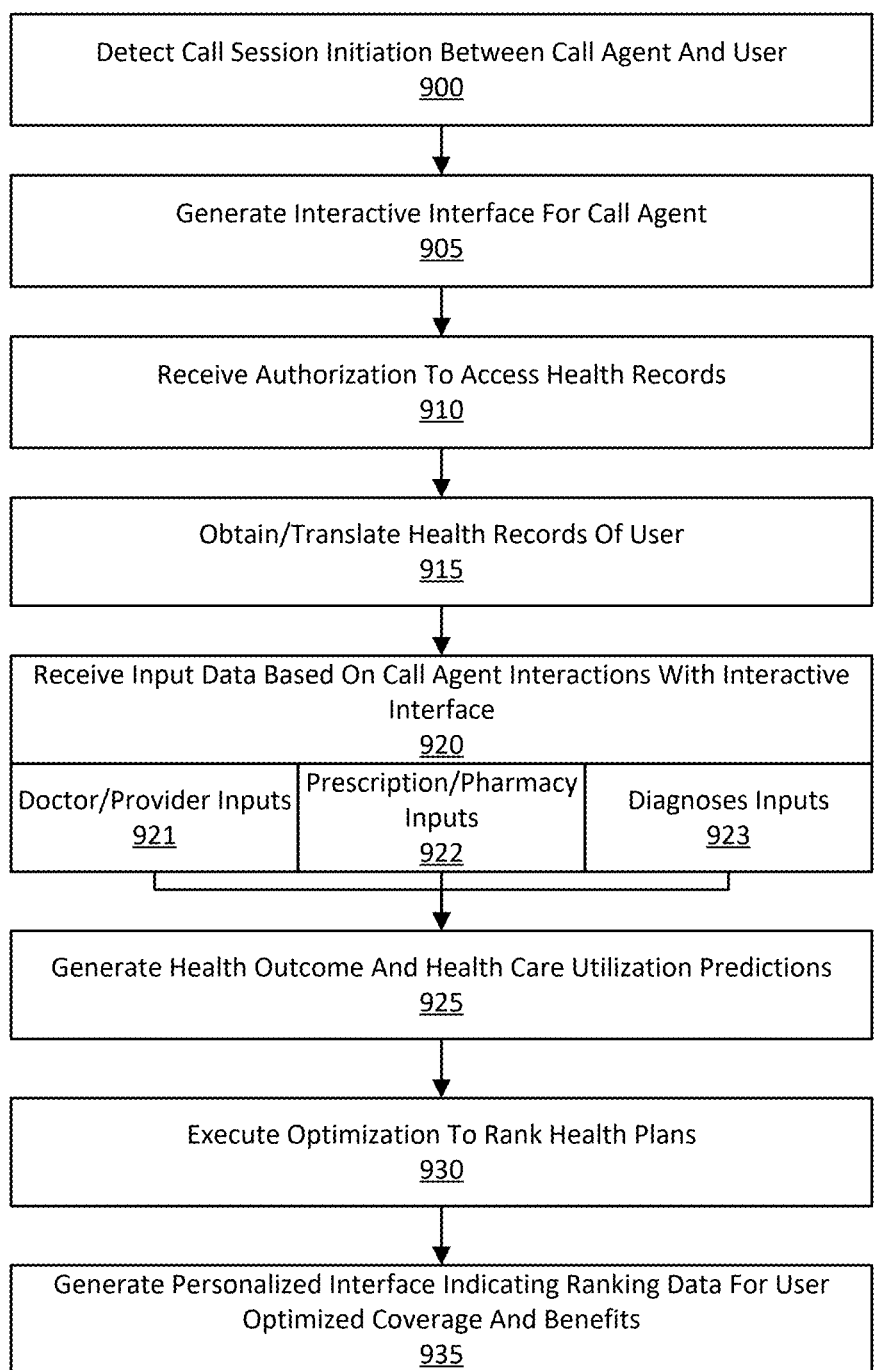
FIG. 9A is a flow chart describing a method of optimizing health plans for users, according to various examples.

FIG. 9A is a flow chart describing a method of optimizing health plans for users, according to various examples. In the below discussion of FIG. 9A, reference may also be made to reference characters representing certain features and components as shown and described with respect to FIGS. 7, 8A, 8B, 8C, and 8D. Furthermore, the processes described with respect to FIG. 9A may be performed by a backend computing system 700, agent computing device 767, or a combination of both. Still further, while the steps in FIG. 9A are shown in a specific order, each step described may be performed prior to, in conjunction with, or subsequent to any other step. Referring to FIG. 9A, the computing system 700 can detect a call session being initiated between a call agent 765 and a user 775 (900). The computing system 700 can further provide data that enables the call agent 765 computing device 767 to generate the interactive agent interface 768 for guiding the call agent 767 during the call session (905). During the call session, the call agent 765 may receive and input the user's authorization to access and/or obtain the user's health records (910).

In various implementations, the computing system 700 can obtain and translate the health records of the user 775 (915). As the call session progresses, the computing system 700 can receive input data based on the call agent's interactions with the interactive agent interface 768 during the call session (920). As described herein, the input data can indicate doctor and health care provider inputs corresponding to the user's current and/or preferred doctors and health care facilities, as inputted by the call agent 765 on the interactive interface 800 shown in FIG. 8B (921). The input data can further correspond to prescription inputs and preferred or necessary pharmacy inputs provided by the call agent 765 on the interactive interface 800 as shown in FIGS. 8A and 8B (922). The input data can further correspond to diagnoses inputs provided by call agent 765 on the interactive interface 800 as shown in FIG. 8C (923).

Based on the input data and health records of the user 775, the computing system 700 can generate health outcome and health care utilization predictions for the user 775 (925). As described herein, the predicted health outcomes can correspond to any future diagnoses based on the user's current diagnoses, treatments, lab results, and/or prescriptions. As further provided herein, the predicted health care utilization of the user 775 can correspond to the predicted future health care needs of the user 775, which can include any future tests, treatments, prescriptions, facility visits, and health care coverage needs. The health prediction engine 735 performing such predictions based on the input data from the call agent 765 and the user's health records can do so using machine learning or artificial intelligence techniques discussed throughout the present disclosure. For example, the health prediction engine 735 can execute an artificial intelligence application trained to compare the user's health records with a corpus of historical health records, filter the historical health records based on the user's personal information, such as age, weight, gender, demographic information, genetics, current diagnoses, medications, and the like. The health prediction engine 735 can identify a set of matching health records in which health outcomes are known, and generate a set of probable health outcome predictions for the user 775, which can include probabilities for future diagnoses, treatments, prescription medications, lab tests, and the like.

In various examples, the computing system 700 includes a ranking engine 740 that can execute an optimizer 742 to rank various health care plans 717 and the individual benefits and attributes of the health care plans 717 based on the user's health outcome predictions, health records, and input data provided by the call agent 765, as described above (930). The computing system 700 may then cause the interactive agent interface 800 to present a personalized interface feature indicating ranked health care plans optimized for coverage and benefits specific to the user 775 (935). In some examples, the interface feature can provide a benefits and attributes comparison between the most optimal health care plan for the user 775 and the user's current health care plan, as shown in FIG. 8D. In further examples, the interface feature can further enable the call agent 765 and/or user 775 to compare other ranked health care plans with the user's current health care plan. The interface feature may further enable the call agent 765 or user 775 to cancel the user's current health care plan and enroll the user in the most optimal health care plan or a plan of the user's choosing.

FIG. 9B is a flow chart describing another method of optimizing health plans for users, according to various examples. In the below discussion of FIG. 9B, reference may also be made to reference characters representing certain features and components as shown and described with respect to FIGS. 7, 8E, 8F, 8G, 8E, and 8H. Furthermore, the processes described with respect to FIG. 9B may be performed by a backend computing system 700, user computing device 770, or a combination of both. Still further, while the steps in FIG. 9B are shown in a specific order, each step described may be performed prior to, in conjunction with, or subsequent to any other step. Referring to FIG. 9B, the computing system 700 can detect an interactive session on a user computing device 770, which can correspond to a user 775 accessing a web portal or health service application (950). The computing system 700 can further receive an authorization input to obtain the user's health records (955). The computing system 700 can then obtain and translate the health records of the user 775 and prepopulate the interactive user interface 778 for the user 775 (960).

According to examples provided herein, the computing system 700 can receive input data based on the user's interactions with the interactive user interface 778 (965). The input data can correspond to the user's interactions with the various screens of the interactive user interface 860 as shown and described with respect to FIGS. 8E through 8H and can include doctor and health care provider inputs (966), prescription inputs and preferred or necessary pharmacy inputs (967), and diagnoses inputs (968). Such inputs can correspond to the user's confirmation of information included in the obtained health records, the user's preferences pertaining to doctors, health care facilities, pharmacies, and medications, and confirmations of the user's diagnoses. Based on the input data and the health records of the user 775, the computing system 700 can generate a set of health outcome and health care utilization predictions for the user 775 (970). The computing system 700 can further process the foregoing data by executing an optimizer 742 to rank the various benefits and attributes of health care plans 717 for the user 775 (975). The computing system 700 can then generate a personalized interface feature that indicates ranking data for user optimized coverage and benefits (980). As provided herein, the personalized interface can enable the user 775 to view ranked benefits and attributes in various health care plans (e.g., a top ten ranking and/or a most optimal health care plan) in comparison to the user's current plan. The personalized interface can further enable the user 775 to selectively enroll in a ranked plan.

Call Agent Computing Device

Figure 10:
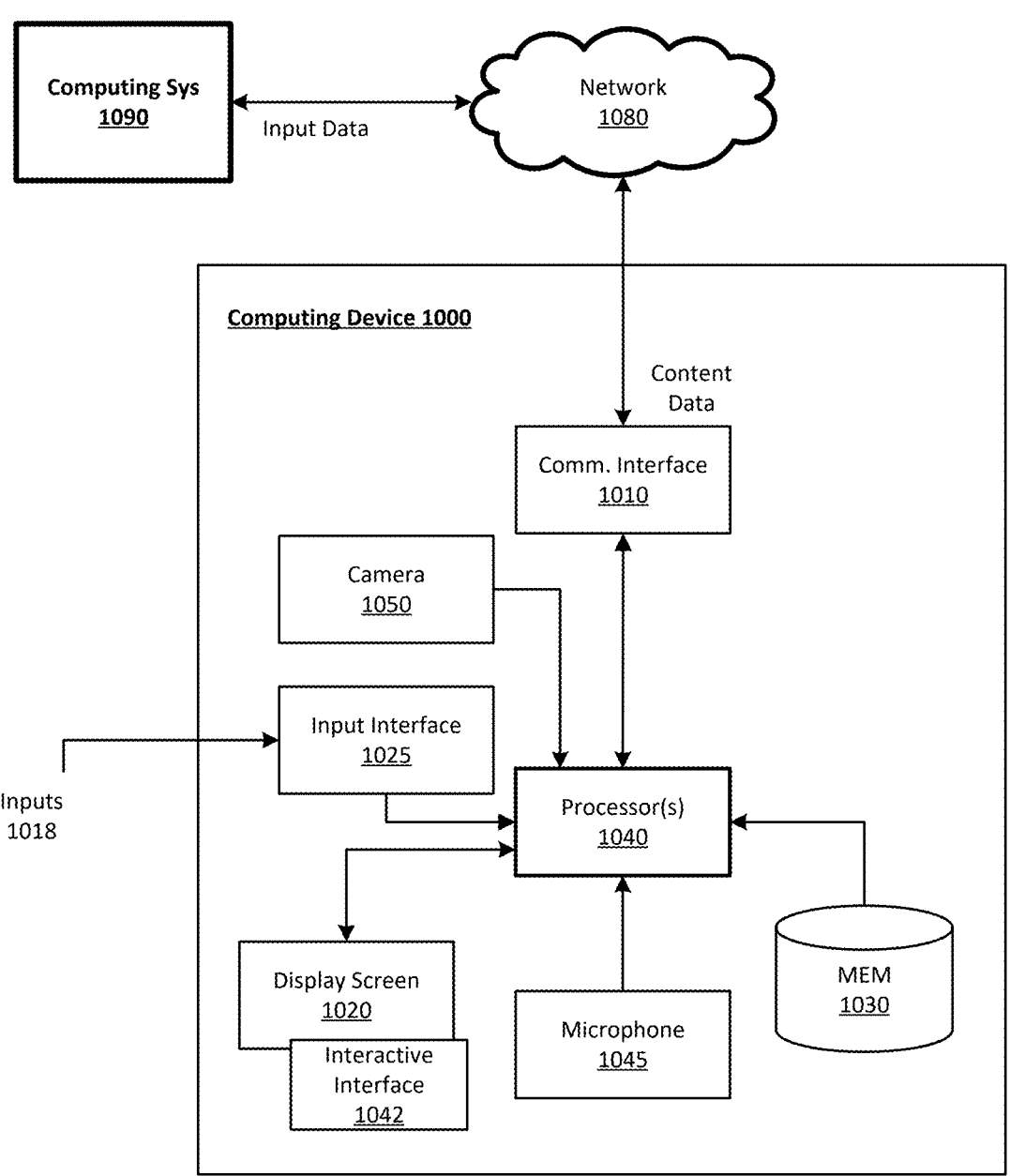
FIG. 10 illustrates a computing device of a call agent communicating in real time with the computing systems described herein, according to examples described herein.

FIG. 10 illustrates a computing device of a call agent communicating in real time with the computing systems described throughout the present disclosure, according to examples described herein. In many implementations, the computing device 1000 can comprise a mobile computing device, such as a smartphone, tablet computer, laptop computer, personal computer, VR or AR headset device, and the like. In certain examples, the computing device 1000 can include telephony features such as a microphone 1045, a camera 1050, and a communication interface 1010 to communicate with the computing system 1090 over one or more networks 1080 using any number of wireless communication protocols.

In certain aspects, the computing device 1000 can store a designated health service application in a local memory 1030 that enables the computing device 1000 to communicate with the computing system 1090. The computing device 1000 can further access one or more networks 1080 via a web browser. In variations, the memory 1030 can store additional applications executable by one or more processors 1040 of the computing device 1000, enabling access and interaction with one or more servers over the one or more networks 1080.

Additionally, the computing device 1000 can be operated by a call agent to perform call sessions with users. In various examples, the call agent can select the health service application via a user input 1018, which can cause the application to be executed by the processor 1040. In response, an interactive agent interface 1042 can be generated on the display screen 1020, which can provide the call agent with all necessary information to perform call sessions as described throughout the present disclosure. During a call session, the call agent can provide inputs 1018 on an input interface 1025 (e.g., the display screen 1020, a keyboard, a keypad, a mouse, etc.) based on the interactions between the call agent and a particular user.

As provided herein, the application and or web browser can enable a communication link over one or more networks 1080 with the computing system 1090, such as the computing systems shown and described throughout the present disclosure. The processor 1040 can generate interactive interface features 1042 using content or display data received from the computing system 1090 over the network 1080. As provided herein, the content data can correspond to prepopulated health record data provided for the call agent, dynamic scripting, health plan rankings, health predictions for the user, health record information of the user, and any additional personal details of the user receive prior to or during the call session.

User Computing Device

Figure 11:
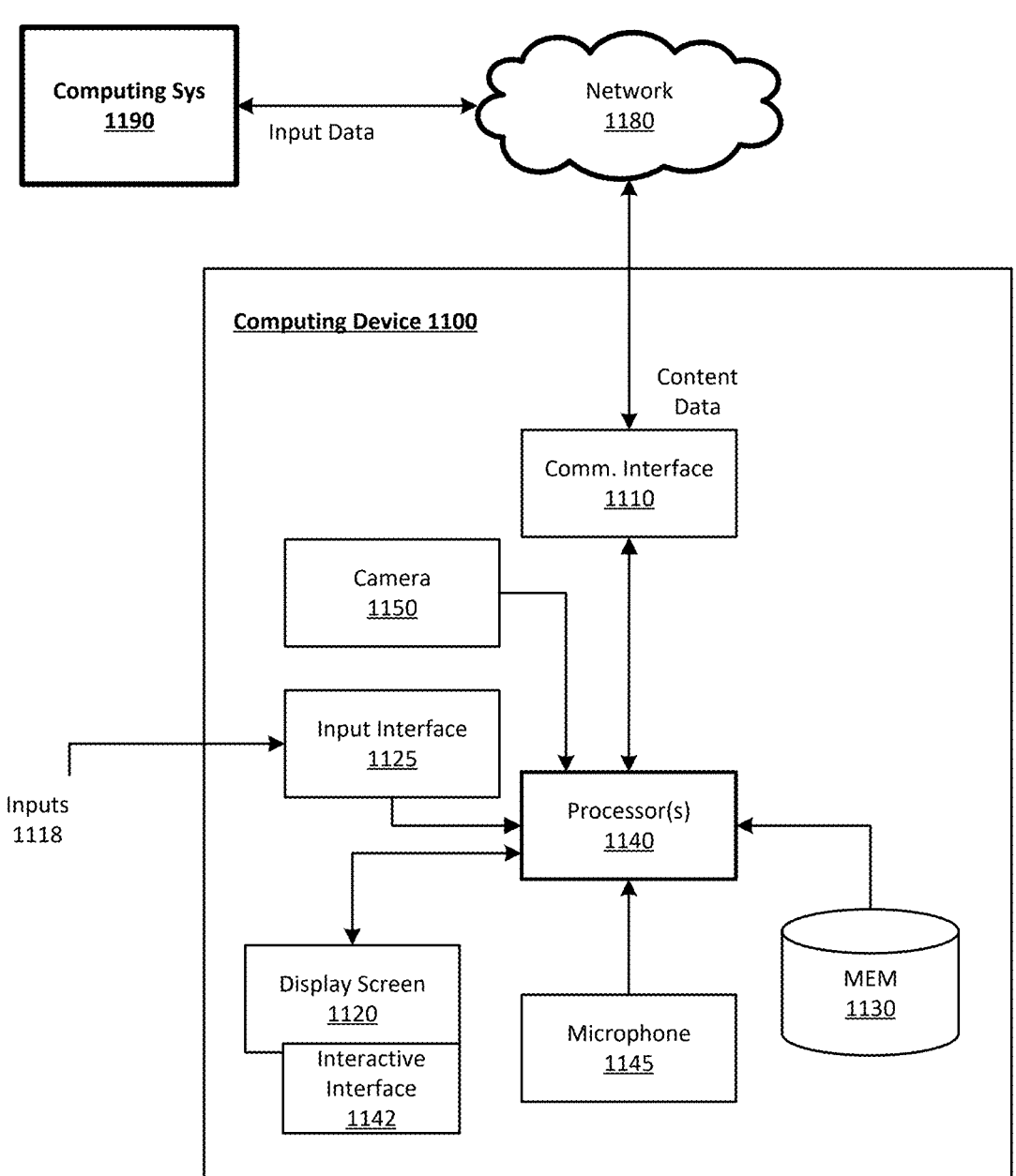
FIG. 11 illustrates a computing device of a user communicating in real time with the computing systems described herein, according to examples described herein.

FIG. 11 illustrates a computing device 1100 for communicating with the computing systems described throughout the present disclosure, according to examples described herein. In many implementations, the computing device 1100 can comprise a mobile computing device, such as a smartphone, tablet computer, laptop computer, personal computer, VR or AR headset device, and the like. In certain examples, the computing device 1100 can include telephony features such as a microphone 1145, a camera 1150, and a communication interface 1110 to communicate with the computing system 1190 using any number of wireless communication protocols. The computing device 1100 can further include a positioning module 1160 (e.g., GPS) and/or an inertial measurement unit that includes one or more accelerometers, gyroscopes, or magnetometers.

In certain aspects, the computing device 1100 can store a designated health service application in a local memory 1130. The computing device 1100 can further access one or more networks 1180 via a web browser. In variations, the memory 1130 can store additional applications executable by one or more processors 1140 of the computing device 1100, enabling access and interaction with one or more servers over the one or more networks 1180.

Additionally, the computing device 1100 can be operated by a user through execution of the health service application or via a website. In various examples, the user can select the health service application or access a health service website via a user input 1118 on the display screen 1120 or input interface 1125, which can cause the application to be executed by the processor 1140 or the website to be presented on the display screen 1120. In response, an interactive user interface 1142 can be generated on the display screen 1120, which can provide access to the health record compilation, verification, and dispute services, as well as the health outcome prediction and planning services described throughout the present disclosure. Alternatively, the interactive interface 1142 can comprise an interactive user interface which the user can navigate to provide inputs corresponding to the input data described in connection with FIG. 7.

As provided herein, the health service application can enable a communication link over one or more networks 1180 with the computing system 1190, such as the computing systems shown and described throughout the present disclosure. The processor 1140 can generate user interface features 1142 using content or display data received from the computing system 1190 over the network 1180. As provided herein, the content data can correspond to translated health records, verification and dispute features, health outcome predictions, health planning features, health plan surveys, enrollment features, etc., as described herein.

Hardware Diagram

Figure 12:
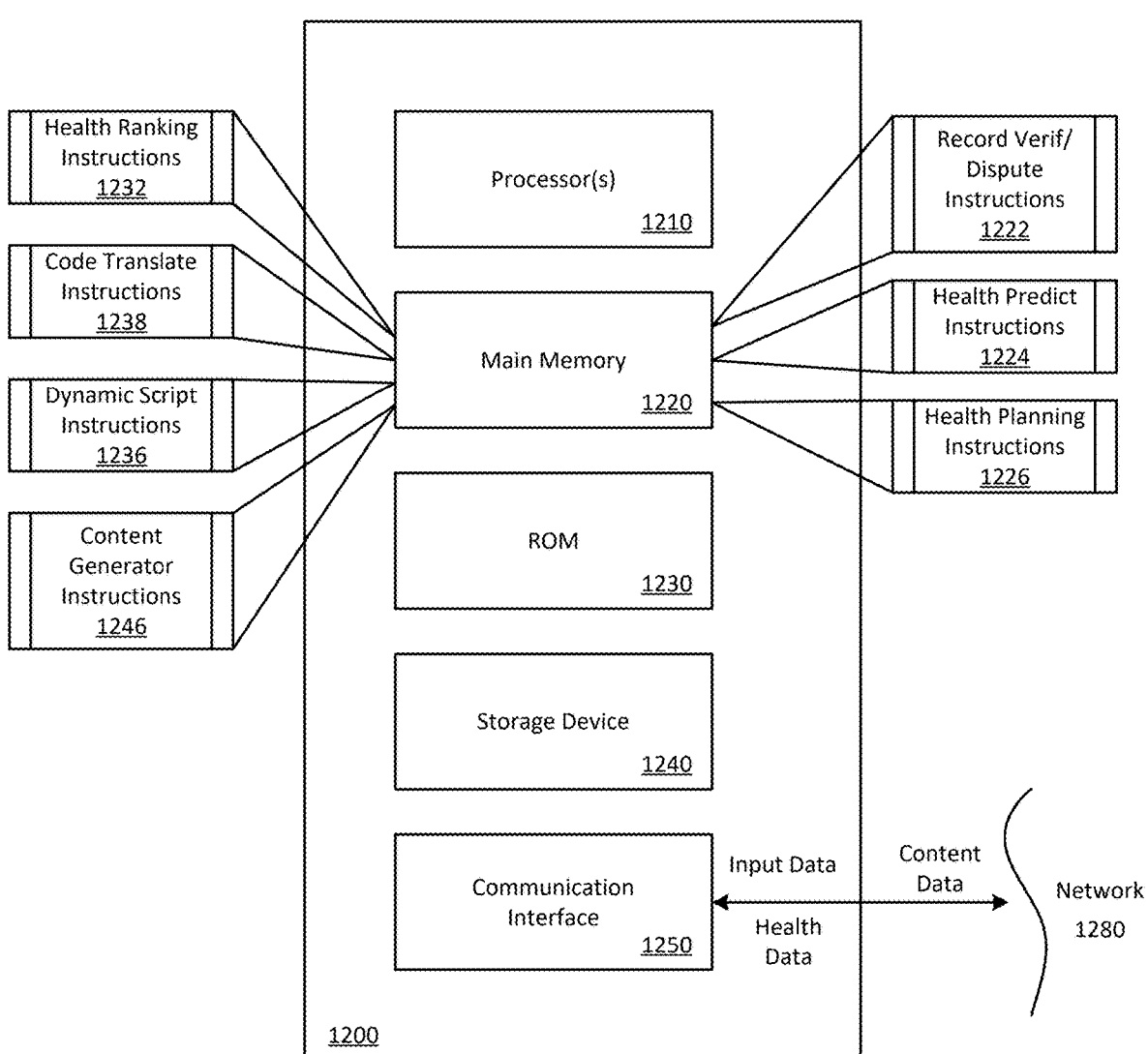
FIG. 12 is a block diagram that illustrates a computer system upon which examples described herein may be implemented.

FIG. 12 is a block diagram that illustrates a computer system 1200 upon which examples described herein may be implemented. A computer system 1200 can be implemented on, for example, computer module, computer server, or a combination of computing device. For example, the computer system 1200 may be implemented as part of a network-based service, such as described throughout the present application. In the context of FIGS. 1, 4, and 7 the computing systems 100, 400, and 700 may be implemented using a computer system 1200 such as described by FIG. 12. While the computing systems 100, 400, 700 of FIGS. 1, 4, and 7 are shown as separate computing systems, as provided herein, the computing systems 100, 400, 700 may operate as a single computer system 1200 or a combination of computer systems 1200 as shown and described with respect to FIG. 12.

In one implementation, the computer system 1200 includes processing resources 1210, a main memory 1220, a read-only memory (ROM) 1230, a storage device 1240, and a communication interface 1250. The computer system 1200 includes at least one processor 1210 for processing information stored in the main memory 1220, such as provided by a random-access memory (RAM) or other dynamic storage device, for storing information and instructions which are executable by the processor 1210. The main memory 1220 also may be used for storing temporary variables or other intermediate information during execution of instructions to be executed by the processor 1210. The computer system 1200 may also include ROM 1230 or other static storage device for storing static information and instructions for the processor 1210. A storage device 1240, such as a magnetic disk or optical disk, is provided for storing information and instructions.

The communication interface 1250 enables the computer system 1200 to communicate with one or more networks 1280 (e.g., cellular network) through use of the network link (wireless or wired). Using the network link, the computer system 1200 can communicate with one or more computing devices, one or more servers, and/or one or more databases. In accordance with examples provided herein, the memory 1220 can store executable instructions, including record verification and dispute instructions 1222, health prediction instructions 1224, and health planning instructions 1226. In accordance with examples provided herein, the memory 1220 can store executable instructions, including dynamic scripting instructions 1236, health record code translation instructions 1238, and health plan ranking instructions 1232. In accordance with examples provided herein, the memory 1220 can further store content generator instructions 1246. The various instructions may comprise programmatic language, machine learning models, artificial intelligence, or any other suitable code for performing the tasks described throughout the present disclosure.

By way of example, the instructions and data stored in the memory 1220 can be executed by the processor 1210 to implement the functions of an example computing system of FIGS. 1, 4, and 7. In various examples, the processor 1210 can execute the health record verification and dispute instructions 1222 to enable a user to verify health records and initiate disputes, as described above. The processors 1210 can further execute the health prediction instructions 1224 to generate a set of health outcome predictions for a user based on the user's health records, as described above. The processors 1210 can further execute the health planning instructions 1226 to generate a set of health plan and lifestyle recommendations, as further described in detail above.

In various examples, the processor 1210 can execute the dynamic scripting instructions 1236 to provide a call agent with a dynamic script for a call session with a user, as described above. The processors 1210 can further execute the code translation instructions 1238 to obtain a user's health records and automatically translate the coded records into plain language. The processors 1210 can further execute the health plan ranking instructions 1232 to score the various attributes of health plans and provide the call agent and/or user with a health plan ranking based on all obtained information. The processors 1210 can further execute the health prediction instructions 1224 to generate a set of health outcome predictions for a user based on the user's health records, as described above.

In various examples, the processor 1210 can execute the content generator instructions 1246 to prepopulate an interactive agent interface for a call agent to reference during a call session with a user, as described above. The processors 1210 can further execute the code translation instructions 1238 to obtain a user's health records and automatically translate the coded records into plain language. The processors 1210 can further execute the health plan ranking instructions 1232 to score the various attributes of health plans and provide the call agent and/or user with a health plan ranking based on all obtained information. The processors 1210 can further execute the health prediction instructions 1224 to generate a set of health outcome predictions for a user based on the user's health records, as described above.

Examples described herein are related to the use of the computer system 1200 for implementing the techniques described herein. According to one example, those techniques are performed by the computer system 1200 in response to the processor 1210 executing one or more sequences of one or more instructions contained in the main memory 1220. Such instructions may be read into the main memory 1220 from another machine-readable medium, such as the storage device 1240. Execution of the sequences of instructions contained in the main memory 1220 causes the processor 1210 to perform the process steps described herein. In alternative implementations, hard-wired circuitry may be used in place of or in combination with software instructions to implement examples described herein. Thus, the examples described are not limited to any specific combination of hardware circuitry and software.

It is contemplated for examples described herein to extend to individual elements and concepts described herein, independently of other concepts, ideas or systems, as well as for examples to include combinations of elements recited anywhere in this application. Although examples are described in detail herein with reference to the accompanying drawings, it is to be understood that the concepts are not limited to those precise examples. As such, many modifications and variations will be apparent to practitioners skilled in this art. Accordingly, it is intended that the scope of the concepts be defined by the following claims and their equivalents. Furthermore, it is contemplated that a particular feature described either individually or as part of an example can be combined with other individually described features, or parts of other examples, even if the other features and examples make no mentioned of the particular feature. Thus, the absence of describing combinations should not preclude claiming rights to such combinations.

What is claimed is:

1. A computing system comprising:
a network communication interface to communicate, over one or more networks, with i) a group of health record computing systems, ii) a computing device of a user, iii) one or more computing systems of one or more health care providers, and iv) one or more databases;
one or more processors; and
at least one memory storing instructions that, when executed by the one or more processors, cause the computing system to:
receive, from the user, respective credential information for the group of health record computing systems that store health record data in a digital format;
receive, from the user, input authorizing access to health record data stored in the group of health record computing systems;
provide remote access, over the one or more networks, to i) the group of health record computing systems, ii) the computing device of the user, and iii) the one or more computing systems of the one or more health care providers, so that any one of i) the group of health record computing systems, ii) the computing device of the user, and iii) the one or more computing systems of the one or more health care providers can update a collection of medical records of the user in real-time;
obtain, over at least one first network of the one or more networks, a collection of health record data of the user from the group of health record computing systems in response to receiving the input authorizing the access to the health record data, the collection of health record data including at least first health record data, second health record data, one or more first health record computing systems of the group of health record computing systems storing the first health record data as first codes in a first coding protocol, one or more second health record computing systems of the group of health record computing systems storing the second health record data as second codes in a second coding protocol,
wherein the first codes and the second codes include different ones of current procedure terminology (CPT) codes, health common procedure coding system (HCPCS) codes, internal classification of diseases (ICD) codes, internal classification of functioning, disability, and health (ICF) codes, diagnostic-related group (DRG) codes, national drug codes (NDC), code on dental procedures and nomenclature (CDT), diagnostic and statistical manual of mental disorder (DSM) codes, national council for prescription drugs (NCPDP) codes, or national provider identifier (NPI codes), and
wherein the first health record data and the second health record data are in a non-standardized format based on the first coding protocol being different from the second coding protocol;
translate, in substantial real-time after obtaining the collection of health record data, A) the first codes of the first health record data from the first coding protocol into a standardized format and B) the second codes of the second health record data from the second coding protocol into the standardized format, the standardized format being a natural language format including plain language descriptors comprising standardized health record data of A) the first codes of the first health record data in the first coding protocol and B) the second codes of the second health record data in the second coding protocol;

store the standardized health record data in the standardized format in at least one of the one or more databases over at least one second network of the one or more networks, the one or more databases having the collection of medical records of the user stored thereon;

generate, for the computing device of the user, an interactive user interface comprising prepopulated data based on the standardized health record data and the collection of health record data;

receive, over at least one third network of the one or more networks from the computing device of the user, first input data provided by the user via the interactive user interface, the first input data corresponding to health-related information provided by the user that updates the health record data of the user in the collection of medical records;

store, in the at least one of the one or more databases and over the at least one second network, the updated health record data of the user in the collection of medical records;

generate a set of health outcome predictions for the user based on the updated health record data;

generate a set of health care plan rankings specific to the user based on the set of health outcome predictions, the first input data, and the collection of health record data, the set of health care plan rankings being displayed via the interactive user interface;

detect one or more triggers for updating the set of health care plan rankings specific to the user, the one or more triggers including receiving, over at least one fourth network of the one or more networks, second input data provided by the one or more computing systems of the one or more health care providers, the second input data corresponding to additional health-related information corresponding to the user that further updates the health record data of the user in the collection of medical records;

store, in the at least one of the one or more databases and over the at least one second network, the further updated health record data of the user in the collection of medical records; and based on the detected one or more triggers and when the further updated health record data has been stored, dynamically update the set of health care plan rankings in accordance with receiving the second input data, wherein the interactive user interface is updated in real-time whenever updated health record data is stored and based on one or more further detected triggers, such that the user has immediate access to up-to-date health information for the user, and wherein the updated health record data is obtained from i) at least one of the group of health record computing systems, ii) the computing device of a user, and/or iii) at least one of the one or more computing systems of the one or more health care providers over at least one of the one or more networks.

2. The computing system of claim 1, wherein the health-related information provided by the user comprises one or more preferred pharmacies of the user.

3. The computing system of claim 1, wherein the health-related information provided by the user comprises one or more preferred doctors or clinics of the user.

4. The computing system of claim 1, wherein the health-related information provided by the user comprises one or more past and current diagnoses of the user.

5. The computing system of claim 1, wherein the health-related information provided by the user comprises one or more past and current medications of the user.

6. The computing system of claim 1, wherein the set of health outcome predictions comprises one or more predicted future diagnoses of the user.

7. The computing system of claim 1, wherein the interactive user interface presents a set of health plan attributes of a highest ranked health care plan for the user.

8. The computing system of claim 7, wherein the interactive user interface presents the set of health plan attributes of the highest ranked health care plan in conjunction with a set of health plan attributes of a current health care plan of the user.

9. A non-transitory computer readable medium storing instructions that, when executed by one or more processors of a computing system, cause the computing system to:

communicate, over one or more networks, with i) a group of health record computing systems, ii) a computing device of a user, iii) one or more computing systems of one or more health care providers, and iv) one or more databases;

receive, from a user, respective credential information for a group of health record computing systems that store health record data in a digital format;

receive, from the user, input authorizing access to health record data stored in the group of health record computing systems;

provide remote access, over the one or more networks, to i) the group of health record computing systems, ii) the computing device of the user, and iii) the one or more computing systems of the one or more health care providers, so that any one of i) the group of health record computing systems, ii) the computing device of the user, and iii) the one or more computing systems of the one or more health care providers can update a collection of medical records of the user in real-time;

obtain, over at least one first network of the one or more networks, a collection of health record data of the user from the group of health record computing systems in response to receiving the input authorizing the access to the health record data, the collection of health record data including at least first health record data, second health record data, one or more first health record computing systems of the group of health record computing systems storing the first health record data as first codes in a first coding protocol, one or more second health record computing systems of the group of health record computing systems storing the second health record data as second codes in a second coding protocol, wherein the first codes and the second codes include different ones of current procedure terminology (CPT) codes, health common procedure coding system (HCPCS) codes, internal classification of diseases (ICD) codes, internal classification of functioning, disability, and health (ICF) codes, diagnostic-related group (DRG) codes, national drug codes (NDC), code on dental procedures and nomenclature (CDT), diagnostic and statistical manual of mental disorder (DSM) codes, national council for prescription drugs (NCPDP) codes, or national provider identifier (NPI codes), and wherein the first health record data and the second health record data are in a non-standardized format based on the first coding protocol being different from the second coding protocol;

translate, in substantial real-time after obtaining the collection of health record data, A) the first codes of the first health record data from the first coding protocol into a standardized format and B) the second codes of the second health record data from the second coding protocol into the standardized format, the standardized format being a natural language format including plain language descriptors comprising standardized health record data of A) the first codes of the first health record data in the first coding protocol and B) the second codes of the second health record data in the second coding protocol;

store the standardized health record data in the standardized format in at least one of the one or more databases over at least one second network of the one or more networks, the one or more databases having the collection of medical records of the user stored thereon;

generate, for the computing device of the user, an interactive user interface comprising prepopulated data based on the standardized health record data and the collection of health record data;

receive, over at least one third network of the one or more networks from the computing device of the user, first input data provided by the user via the interactive user interface, the first input data corresponding to health-related information provided by the user that updates the health record data of the user in the collection of medical records;

store, in the at least one of the one or more databases and over the at least one second network, the updated health record data of the user in the collection of medical records;

generate a set of health outcome predictions for the user based on the updated health record data;

generate a set of health care plan rankings specific to the user based on the set of health outcome predictions, the first input data, and the collection of health record data, the first-set of health care plan rankings being displayed via the interactive user interface;

detect one or more triggers for updating the set of health care plan rankings specific to the user, the one or more triggers including receiving, over at least one fourth network of the one or more networks, second input data provided by the one or more computing systems of the one or more health care providers, the second input data corresponding to additional health-related information corresponding to the user that further updates the health record data of the user in the collection of medical records;

store, in the at least one of the one or more databases and over the at least one second network, the further updated health record data of the user in the collection of medical records; and based on the detected one or more triggers and when the further updated health record data has been stored, dynamically update the set of health care plan rankings in accordance with receiving the second input data, wherein the interactive user interface is updated in real-time whenever updated health record data is stored and based on one or more further detected triggers, such that the user has immediate access to up-to-date health information for the user, and wherein the updated health record data is obtained from i) at least one of the group of health record computing systems, ii) the computing device of a user, and/or iii) at least one of the one or more computing systems of the one or more health care providers over at least one of the one or more networks.

10. The non-transitory computer readable medium of claim 9, wherein the health-related information provided by the user comprises one or more preferred pharmacies of the user.

11. The non-transitory computer readable medium of claim 9, wherein the health-related information provided by the user comprises one or more preferred doctors or clinics of the user.

12. The non-transitory computer readable medium of claim 9, wherein the health-related information provided by the user comprises one or more past and current diagnoses of the user.

13. The non-transitory computer readable medium of claim 9, wherein the health-related information provided by the user comprises one or more past and current medications of the user.

14. The non-transitory computer readable medium of claim 9, wherein the set of health outcome predictions comprises one or more predicted future diagnoses of the user.

15. The non-transitory computer readable medium of claim 9, wherein the interactive user interface presents a set of health plan attributes of a highest ranked health care plan for the user.

16. The non-transitory computer readable medium of claim 15, wherein the interactive user interface presents the set of health plan attributes of the highest ranked health care plan in conjunction with a set of health plan attributes of a current health care plan of the user.

17. A computer-implemented method, comprising:

communicating, over one or more networks, with i) a group of health record computing systems, ii) a computing device of a user, iii) one or more computing systems of one or more health care providers, and iv) one or more databases;

receiving, from the user, respective credential information for the group of health record computing systems that store health record data in a digital format;

receiving, from the user, input authorizing access to health record data stored in the group of health record computing systems;

providing remote access, over the one or more networks, to i) the group of health record computing systems, ii) the computing device of the user, and iii) the one or more computing systems of the one or more health care providers, so that any one of i) the group of health record computing systems, ii) the computing device of the user, and iii) the one or more computing systems of the one or more health care providers can update a collection of medical records of the user in real-time;

obtaining, over at least one first network of the one or more networks, a collection of health record data of the user from the group of health record computing systems in response to receiving the input authorizing the access to the health record data, the collection of health record data including at least first health record data, second health record data, one or more first health record computing systems of the group of health record computing systems storing the first health record data as first codes in a first coding protocol, one or more second health record computing systems of the group of health record computing systems storing the second health record data as second codes in a second coding protocol, wherein the first codes and the second codes include different ones of current procedure terminology (CPT) codes, health common procedure coding system (HCPCS) codes, internal classification of diseases (ICD) codes, internal classification of functioning, disability, and health (ICF) codes, diagnostic-related group (DRG) codes, national drug codes (NDC), code on dental procedures and nomenclature (CDT), diagnostic and statistical manual of mental disorder (DSM) codes, national council for prescription drugs (NCPDP) codes, or national provider identifier (NPI codes), and wherein the first health record data and the second health record data are in a non-standardized format based on the first coding protocol being different from the second coding protocol;

translating, in substantial real-time after obtaining the collection of health record data, A) the first codes of the first health record data from the first coding protocol into a standardized format and B) the second codes of the second health record data from the second coding protocol into the standardized format, the standardized format being a natural language format including plain language descriptors comprising standardized health record data of A) the first codes of the first health record data in the first coding protocol and B) the second codes of the second health record data in the second coding protocol;

storing the standardized health record data in the standardized format in at least one of the one or more databases over at least one second network of the one or more networks, the one or more databases having the collection of medical records of the user stored thereon;

generating, for the computing device of the user, an interactive user interface comprising prepopulated data based on the standardized health record data and the collection of health record data;

receiving, over at least one third network of the one or more networks from the computing device of the user, first input data provided by the user via the interactive user interface, the first input data corresponding to health-related information provided by the user that updates the health record data of the user in the collection of medical records;

storing, in the at least one of the one or more databases and over the at least one second network, the updated health record data of the user in the collection of medical records;

generating a set of health outcome predictions for the user based on the updated health record data;

generating a set of health care plan rankings specific to the user based on the set of health outcome predictions, the first input data, and the collection of health record data, the set of health care plan rankings being displayed via the interactive user interface;

detecting one or more triggers for updating the set of health care plan rankings specific to the user, the one or more triggers including receiving, over at least one fourth network of the one or more networks, second input data provided by the one or more computing systems of the one or more health care providers, the second input data corresponding to additional health-related information corresponding to the user that further updates the health record data of the user in the collection of medical records;

storing, in the at least one of the one or more databases and over the at least one second network, the further updated health record data of the user in the collection of medical records; and based on the detected one or more triggers and when the further updated health record data has been stored, dynamically updating the set of health care plan rankings in accordance with receiving the second input data, wherein the interactive user interface is updated in real-time whenever updated health record data is stored and based on one or more further detected triggers, such that the user has immediate access to up-to-date health information for the user, and wherein the updated health record data is obtained from i) at least one of the group of health record computing systems, ii) the computing device of a user, and/or iii) at least one of the one or more computing systems of the one or more health care providers over at least one of the one or more networks.

18. The method of claim 17, further comprising:

automatically generating a message including the updated health record data of the user whenever updated health record data of the user has been stored; and transmitting the message to the computing device of the user in real-time, over the at least one third network, such that the user has immediate access to the up-to-date health information for the user.

19. The method of claim 17, further comprising:

based on the one or more further detected triggers, automatically further updating the dynamically updated set of health care plans for the user in real-time whenever updated health record data of the user has been stored, such that the user has immediate access to up-to-date health plan information for the user.

20. The method of claim 19, further comprising:

automatically generating a message including the further updated dynamically updated set of health care plans for the user whenever updated health record data of the user has been stored and based on the one or more further detected triggers; and transmitting the message to the computing device of the user over the at least one third network in real-time, such that the user has immediate access to the up-to-date health plan information for the user.

* * * * *